US007898255B2

(12) United States Patent
Ochi et al.

(10) Patent No.: US 7,898,255 B2
(45) Date of Patent: Mar. 1, 2011

(54) INSPECTION APPARATUS USING MAGNETIC RESONANCE AND NUCLEAR MAGNETIC RESONANCE SIGNAL RECEIVER COIL

(75) Inventors: Hisaaki Ochi, Kodaira (JP); Yo Taniguchi, Kokubunji (JP); Hiroyuki Takeuchi, Kashiwa (JP)

(73) Assignees: Hitachi, Ltd., Tokyo (JP); Hitachi Medical Corporation, Chiba (JP)

( * ) Notice: Subject to any disclaimer, the term of this patent is extended or adjusted under 35 U.S.C. 154(b) by 881 days.

(21) Appl. No.: 11/813,011

(22) PCT Filed: Feb. 6, 2006

(86) PCT No.: PCT/JP2006/301983
§ 371 (c)(1),
(2), (4) Date: Jun. 28, 2007

(87) PCT Pub. No.: WO2006/114923
PCT Pub. Date: Nov. 2, 2006

(65) Prior Publication Data
US 2010/0033177 A1    Feb. 11, 2010

(30) Foreign Application Priority Data
Apr. 25, 2005   (JP) ................. 2005-126691

(51) Int. Cl.
*G01V 3/00* (2006.01)
(52) U.S. Cl. ........................ 324/318; 324/322
(58) Field of Classification Search .......... 324/318, 324/322
See application file for complete search history.

(56) References Cited

U.S. PATENT DOCUMENTS

| 5,951,474 | A  | * | 9/1999 | Matsunaga et al. ........... 600/422 |
| 6,777,937 | B1 |   | 8/2004 | Miller et al. |
| 6,914,432 | B2 | * | 7/2005 | Dumoulin et al. ............ 324/318 |
| 7,061,242 | B2 |   | 6/2006 | Ochi et al. |
| 7,394,253 | B2 | * | 7/2008 | Okamoto et al. ............. 324/318 |

(Continued)

FOREIGN PATENT DOCUMENTS
GB    2 289 344    11/1995

(Continued)

OTHER PUBLICATIONS

J. B. Ra, C. Y. Rim : "Fast Imaging Using Subencoding Data Sets from Multiple Detectors", Magnetic Resonance in Medicine, vol. 30, pp. 142-145(1993).

(Continued)

*Primary Examiner* — Louis M Arana
(74) *Attorney, Agent, or Firm* — Antonelli, Terry, Stout & Kraus, LLP.

(57) ABSTRACT

An MRI apparatus capable of selecting an optional direction as a phase encoding direction and achieving a preferable S/N, when an imaging time shortening technique is applied. A receiver coil, used as a receiver coil of a vertical magnetic field MRI apparatus, is a combination of a first coil (solenoid coil) forming a current loop around the outer circumference of a test object, second coils forming even-numbered current loops, and third coils forming odd-numbered current loops, in the direction intersecting the plane of the current loop of the first coil. The second coil and the third coil are arranged in such a manner that, as for the current loops in the array direction thereof, a position where a sensitivity of one coil is minimized approximately coincides with a position where the sensitivity of the other coil is maximized, whereby electromagnetic coupling is suppressed.

14 Claims, 24 Drawing Sheets

U.S. PATENT DOCUMENTS 7,545,144 B2 * 6/2009 Guan et al. .................. 324/318
2004/0196042 A1 10/2004 Fujita et al.

FOREIGN PATENT DOCUMENTS

| JP | 2000-254109 | 9/2000 |
| JP | 2002-153440 | 5/2002 |
| JP | 2003-153878 | 5/2003 |
| JP | 2004-514486 | 5/2004 |
| JP | 2004-196042 | 7/2004 |

OTHER PUBLICATIONS

P. B. Roemer, W. A. Edelstein, C. E. Hayes, S. P. Souza, and O. M. Mueller, : "The NMR Phased Array", Magnetic Resonance in Medicine, vol. 16, pp. 192-225(1990).

Klaas P. Pruessmann, Markus Weiger, Markus B.Scheidegger, and Peter Boesiger : "SENSE: Sensitivity Encoding for Fast MRI", Magnetic Resonance in Medicine, vol. 42, pp. 952-962 (1999).

* cited by examiner (A)

(B)

(A)

(B)

INSPECTION APPARATUS USING MAGNETIC RESONANCE AND NUCLEAR MAGNETIC RESONANCE SIGNAL RECEIVER COIL

TECHNICAL FIELD

The present invention relates to an inspection apparatus using magnetic resonance (hereinafter, referred to as "MRI apparatus"), and more particularly, it relates to a receiver RF coil for detecting a nuclear magnetic resonance signal.

BACKGROUND ART

An MRI apparatus obtains a signal from a test object (a subject being tested) by nuclear magnetic resonance, and produces an image, the subject being placed in a uniform magnetic field. A field of view (FOV) is limited to a uniform magnetic field space generated from a static magnetic field magnet. However, in recent years, an imaging method has been developed, which acquires an image while moving a table with a subject placed thereon, and this enables an imaging of wide field, for example, the whole body of the subject. Imaging the wide field along with such movement of the table as described above needs shortening of imaging time, since a measuring time has to be within a range acceptable by the subject.

As a high-speed imaging method to achieve such reduction of imaging time, there has been developed a technique (referred to as "parallel imaging" or the like, but here referred to as "imaging time shortening technique"), which uses a receiver coil made up of multiple sub-coils and carries out imaging with a wider phase encoding step than a normal phase encoding, whereby aliasing generated in the image are eliminated by utilizing sensitivity distribution information of multiple receiver coils (non-patent document 1). In this imaging method, the number of phase encoding steps can be reduced compared to the normal imaging, and therefore, the imaging time as a whole can be shortened. In theory, thinning-out rate of the phase encoding (=number of phase encoding after thinning-out/number of normal phase encoding) can be assumed as 1/[number of sub-coils], and it is possible to shorten the imaging time in accordance with the thinning-out rate of the phase encoding.

In order to achieve such imaging time shortening technique, first of all, it is necessary that electromagnetic coupling between each of the multiple sub-coils is sufficiently small. If there is an electromagnetic coupling between sub-coils, noises interfere with each other between the sub-coils, and S/N ratio of an image may be deteriorated. Non-patent document 2 discloses a method that utilizes an amplifier with low input impedance for detecting a signal, as a way to suppress the electromagnetic coupling between the two coils. However, this only way is not able to suppress the magnetic coupling completely, if the size of the coil is large relative to a distance between the two coils.

In the imaging time shortening technique, it is required that geometric arrangement of multiple sub-coils is adequately provided. If the geometric arrangement of the multiple sub-coils is not appropriate, the S/N ratio of the image may be partially deteriorated. Specifically, it is desirable that in the geometric arrangement of the multiple sub-coils, a combination of sensitive distributions of the receiver coils covers the imaging area, and these distributions widely differ from one another as possible. As a standard to evaluate the arrangement of the coils, there is a standard called as "g-factor". This g-factor can be obtained according to the following expression (non-patent document 3).

$$G=\sqrt{\{(S^H\Psi^{-1}S)^{-1}(S^H\Psi^{-1}S)\}} \geq 1 \qquad \text{[Expression 1]}$$

In the expression, when the receiver coil has coils, the number of which is indicated by "nc" and the overlapping number of which is indicated by "np", sensitivity matrix (np×nc) of the overlapping positions is represented by "S", and the superscript "H" represents a transposed complex conjugate. $\Psi$ represents the noise matrix (nc×nc) of the receiver coil.

The g-factor, which is a value equal to 1 (one) or more, expresses to what extent the pixels being overlapped due to aliasing can be separated, in the coil configuration being utilized.

Accordingly, with regard to the receiver coil used in the imaging time shortening technique, the electromagnetic coupling between the sub-coils and reduction of the g-factor are critical issues.

Conventionally, as for the imaging time shortening technique, a development has been made mainly in the horizontal magnetic field apparatus having a high magnetic field. Various techniques have been proposed for a configuration of the receiver coil that is suitable for the horizontal magnetic field apparatus. In an MRI apparatus, an RF magnetic field in the direction orthogonal to the static magnetic field (z direction) is detected, and generally in the horizontal magnetic field apparatus, the direction of the static magnetic field corresponds to the body axis direction of the subject. Therefore, surface coils 26-1 to 26-10 as shown in FIG. 26(A) to (C) are used as the receiver coils for use in the horizontal magnetic field apparatus. In the surface coils as shown in (A), there are sub-coils in the x-direction and in the y-direction, with different sensitivity distributions, respectively. Therefore, if either the x-direction or y-direction is selected as a phase encoding direction of an MR image, it is possible to remove aliasing of the image. In addition, in the surface coils as shown in (B) and (C), there are sub-coils in three directions x, y, and z, with sensitivity distributions different respectively. Therefore, it is possible to remove the image aliasing, whichever direction is selected as the phase encoding direction.

In addition, as shown in FIG. 27, a combination of various types of coils is proposed as a receiver coil for use in the horizontal magnetic field apparatus (patent document 1). As for this receiver coil, the coils 27-1 and 27-3 are arranged symmetrically with respect to z-axis, thereby avoiding electromagnetic coupling. Moreover, the direction of the magnetic field generated by the coils 27-2 is in the y-direction, and the direction of the magnetic field generated in areas where the coil 27-1 and the coil 27-3 overlap the coils 27-2 is mainly in the x-direction. Therefore, the electromagnetic coupling is weak among them.

On the other hand, as for a vertical magnetic field apparatus, the direction of the static magnetic field is vertical, and in general, the subject is placed so that its body axis is directed to be orthogonal to the static magnetic field. Therefore, a solenoid coil that is arranged around the outer circumference of the subject is used as the receiver coil. The solenoid coil arranged around the outer circumference of the subject has a sensitivity that is intense even in a deep part of the object, unlike the loop coil placed on the surface of the subject. Therefore, if the magnetic field strength is the same, the vertical magnetic field type MRI in which the solenoid coil is available, provides generally a higher sensitivity in the deep part of the object, compared to the horizontal magnetic field type MRI. As the receiver coil for use in the vertical magnetic field apparatus, the patent document 2 discloses, as shown in FIG. 28, a combination of multiple number of solenoid coils 28-1, 28-2, and 28-3 which are arranged around the outer circumference of the subject, and surface coils 29-1 and 29-2. It further discloses that by use of this receiver coil, highly sensitive and high-speed imaging of an area near the heart in the deep part of the subject is performed, by applying the imaging time shortening technique as described in the non-patent document 1.

This receiver coil is effective in imaging a local region such as area in proximity to the heart, however, it is difficult to apply this receiver coil to the wide field imaging, along with movement of the table as described above.

[Non-Patent Document 1]
J. B. Ra, C. Y. Rim: "Fast Imaging Using Subencoding Data Sets from Multiple Detectors", Magnetic Resonance in Medicine, vol. 30, pp. 142-145 (1993)
[Non-Patent Document 2]
P. B. Roemer, W. A. Edelstein, C. E. Hayes, S. P. Souza, and O. M. Mueller, "The NMR Phased Array", Magnetic Resonance in Medicine, vol. 16, pp. 192-225 (1990)
[Non-Patent Document 3]
Klaas P. Pruessmann, Markus Weiger, Markus B. Scheidegger, and Peter Boesiger: "SENSE: Sensitivity Encoding for Fast MRI", Magnetic Resonance in Medicine, vol. 42, pp. 952-962 (1999)
[Patent Document 1]
US Published Unexamined Patent Application No. 20040196042
[Patent Document 2]
Japanese Published Unexamined Patent Application No. 2002-153440

DISCLOSURE OF THE INVENTION

Problem to be Solved by the Invention

An object of the present invention is to provide a receiver coil used in a vertical magnetic field, being suitable for the imaging time shortening technique and for imaging a wide field along with the application of the technique, and the receiver coil achieves small g-factor in the entire imaging section, whichever phase encoding direction is selected, and further to provide an MRI apparatus incorporating this receiver coil.

Means to Solve the Problem

In order to solve the problem above, an MRI apparatus according to the present invention includes, a unit for generating a static magnetic field in a vertical direction, a unit for generating an excitation RF pulse that is applied to a test object placed in the static magnetic field, a unit for generating a magnetic field gradient that is superimposed on the static magnetic field, a receiver coil that is made up of multiple sub-coils and that detects a nuclear magnetic resonance signal generated from the test object, the multiple sub-coils further including, a first coil that is placed within a plane including an axis parallel to a direction of the static magnetic field, and forms a current loop around an outer circumference of the test object, a second coil that forms even-numbered current loops in a plane intersecting the plane having the current loop of the first coil, and a third coil that forms odd-numbered current loops in a plane approximately parallel to the plane having the current loops of the second coil, wherein, the second coil and the third coil are arranged in such a manner that an array direction of the current loops formed by the second coil is equal to the array direction of the current loops formed by the third coil, and in the array direction of the current loops, a position where a sensitivity of the second coil is minimized approximately coincides with a position where the sensitivity of the third coil is maximized.

The MRI apparatus according to the present invention is provided with the multiple sub-coils constituting the receiver coil, further including, a first coil that is placed in a plane including an axis parallel to a direction of the static magnetic field, and forms a current loop around the outer circumference of the test object, a second coil that forms even-numbered current loops in a plane intersecting the plane of the current loop of the first coil, and a third coil that forms odd-numbered current loops in a plane approximately parallel to the plane of the current loops of the second coil, wherein, the second coil and the third coil are arranged in such a manner as having an approximately identical array direction of the current loops, and with respect to the array direction, centers of the current loops are alternately placed.

The MRI apparatus according to the present invention may have a configuration that more than one sub-coils of at least either of the second coil and the third coil, are arranged in a direction intersecting the array direction of the current loops. The MRI apparatus according to the present invention may further have a configuration that the sub-coils of at least either of the second coil and the third coil are arranged in two approximately parallel planes, placing the test object therebetween. For this case, it is preferable that the sub-coils in pairs placed in the approximately parallel planes putting the test object therebetween are arranged at positions different from each other with respect to an axis orthogonal to the plane of the current loops.

In a preferable aspect of the MRI apparatus according to the present invention, the second coil and the third coil are arranged so that the current loops thereof are displaced from each other in the direction orthogonal to the array direction of the current loops. The second coil may include, for example, two current loops, and the third coil may include, for example, three current loops.

In the MRI apparatus according to the present invention, the receiver coil may have a fourth coil, as sub-coils, which forms current loops respectively on multiple planes parallel to the plane of the current loop of the first coil. In the MRI apparatus according to the present invention, more than one first coils may be arranged in a direction orthogonal to the plane of the current loop. In the case above, by way of example only, the receiver coil may have a unit to electromagnetically disconnect each of the multiple first coils.

A nuclear magnetic resonance signal receiver coil according to the present invention includes, a first coil that is placed in a plane including an axis parallel to a direction of static magnetic field applied from outside, and forms a current loop around an outer circumference of a test object, a second coil that forms even-numbered current loops in a plane intersecting the plane of the current loop of the first coil, and a third coil that forms odd-numbered current loops in a plane approximately parallel to the plane of the current loops of the second coil, wherein, the second coil and the third coil are arranged in such a manner that an array direction of the current loops formed by the second coil is equal to the array direction of the current loops formed by the third coil, and in the array direction of the current loops, a position where a sensitivity of the second coil is minimized approximately coincides with a position where the sensitivity of the third coil is maximized. Alternatively, the second coil and the third coil are arranged in such a manner as having an approximately identical array direction of the current loops, and with respect to the array direction, centers of the current loops are alternately placed.

EFFECT OF THE INVENTION

According to the present invention, there is provided a receiver coil made up of three types of sub-coils, electromagnetic coupling among which is suppressed, and they are arranged appropriately, whereby an image without any deterioration of S/N ratio can be obtained, in the case where an imaging time shortening technique is employed. In addition, three types of sub-coils are configured in such a manner that more than one of each are arranged, for instance, in the body-axis direction of the test object (subject), thereby enabling a selection of any directions x, y, and z, as a phase encoding direction. Therefore, flexibility in imaging is increased and this is applicable to imaging a wide field along with a table movement. Accordingly, in the wide field imaging with the table movement, the imaging time can be shortened dramatically.

BEST MODE FOR CARRYING OUT THE INVENTION

Figure 1:
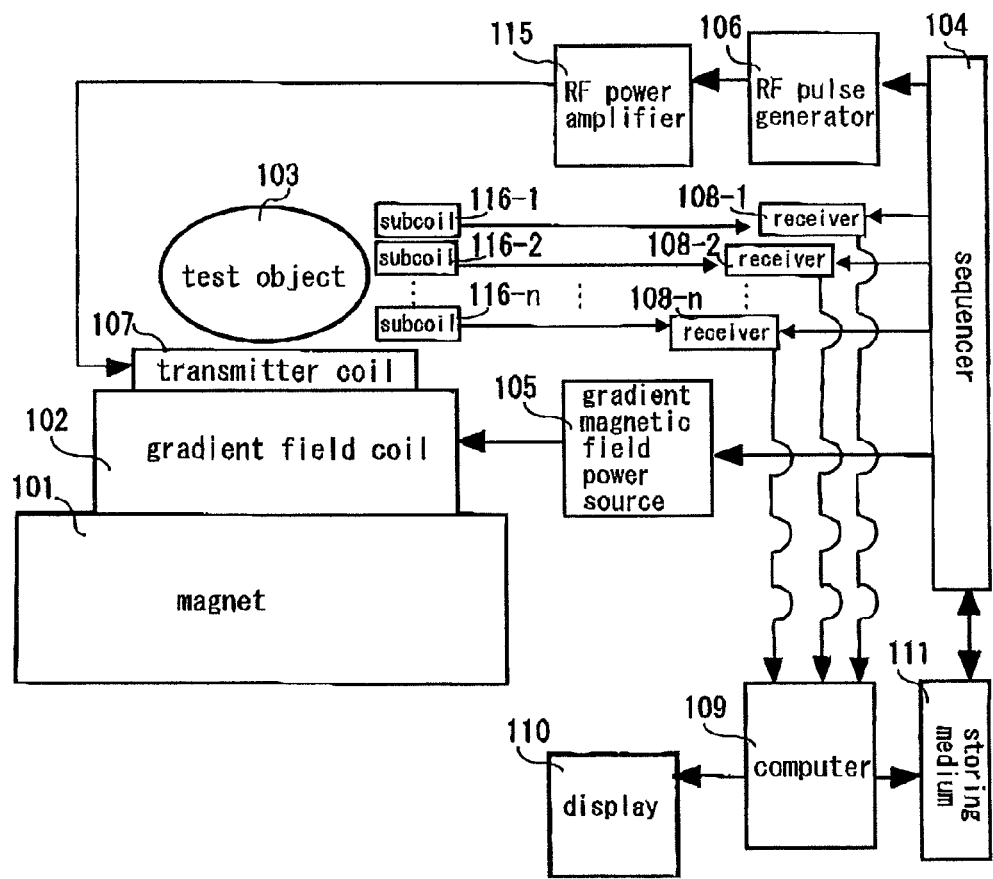
FIG. 1 illustrates an overall structure of an MRI apparatus to which the present invention is applied.
Figure 29:
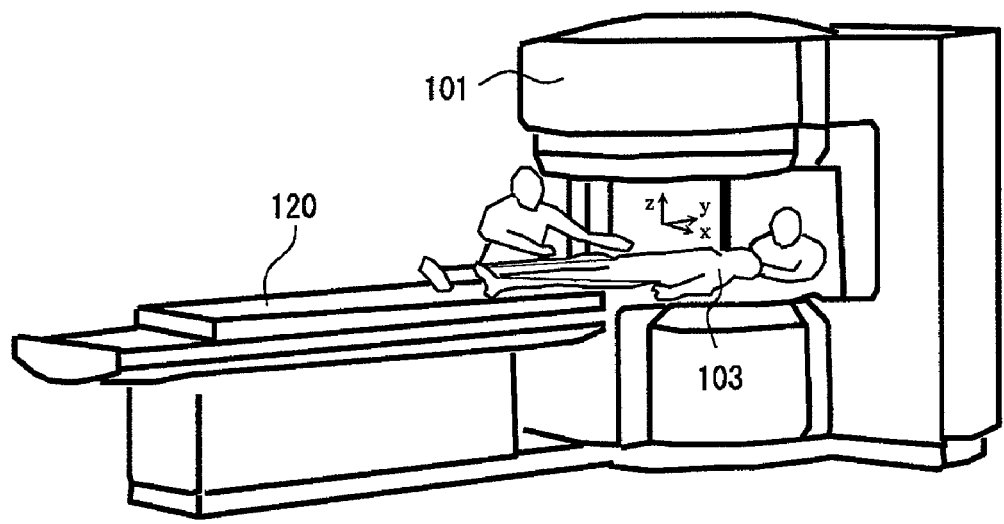
FIG. 29 illustrates an open-type MRI apparatus.

Hereinafter, an embodiment of the present invention will be explained with reference to the accompanying drawings. FIG. 1 is a block diagram showing an overall structure of a vertical magnetic field type MRI apparatus to which the present invention is applied. FIG. 29 is an external view of the apparatus. This MRI apparatus is provided with a magnet 101 that generates a static magnetic field in the vertical direction (hereinafter in the present invention, an explanation will be made assuming the direction of the static magnetic field as "z-direction"), a gradient field coil 102 that generates a magnetic field gradient, a test object (a subject to be tested) 103, a transmitter coil 107 that generates an RF pulse to be applied to a human body, for instance, a receiver coil 116 that receives a nuclear magnetic resonance (NMR) signal generated from the subject 103, a sequencer 104 that controls imaging operations, a computer 109 that subjects the NMR signal received by the receiver coil 116 to signal processing, and performs various calculations required for image restructuring, a table (FIG. 29, reference numeral 120) to carry the subject 103 into the static magnetic field generated by the magnet 101, and the like. The subject 103 is carried into the space of the static magnetic field while being placed on the table.

A publicly known magnet device, such as a permanent magnet, normal conducting magnet, and superconducting magnet, is employed as the magnet 101. The gradient field coil 102 is to provide a magnetic field gradient in the static magnetic field generated by the magnet 101, and it is made up of three gradient field coils each generating the gradient magnetic field in three axial directions (e.g., x, y, and z directions) that are orthogonal to one another. The sequencer 104 operates the control to drive a gradient magnetic field power source 105 in the three axial directions, and a magnetic field gradient is generated in a desired direction. An imaging section of the subject can be determined by the way how the gradient magnetic field is supplied, and positional information can be added to an NMR signal. Further, in order to enhance the uniformity of the static magnetic field, a shim coil is arranged as required. The gradient field coil may also serve as a part of the shim coil.

The transmitter coil 107 is connected to an RF pulse generator 106 via an RF power amplifier 115. An RF pulse outputted from the RF pulse generator 106 according to an instruction from the sequencer 104, is amplified by the RF power amplifier 115, and applied to the subject 103 via the transmitter coil 107.

The receiver coil 116 receives an NMR that is generated from the subject 103 in response to the RF pulse transmission. In the present invention, the receiver coil 116 is made up of multiple sub-coils 116-1 to 116-$n$, and each of them is connected to a receiver 108 having a circuit for A/D conversion and detection. It is to be noted that as for some sub-coils, multiple sub-coils may be connected to one receiver 108 via a switching unit, and through the use of the switching unit, a signal is inputted into the receiver 108 selectively from one of the sub-coils. A center frequency (magnetic resonance frequency), which is used as a standard for detection in the receiver, is set by the sequencer 104.

The signals received by the receiver coil 106 and detected by the receiver 108 are sent to the computer 109 and subjected to resampling, and further subjected to signal processing such as image processing. Measuring conditions and images as the result of the signal processing are stored in a storing medium 111 as appropriate.

The sequencer 104 takes controls so that each unit is operated at a programmed timing and strength. Among the programs, descriptions regarding the application of the RF pulse, the application of the gradient magnetic field, the timing of receiving the nuclear magnetic resonance signal, and the intensity of the RF pulse and gradient magnetic field, are particularly referred to as an imaging sequence.

Next, an explanation will be made regarding the receiver coil for the MRI apparatus having the configuration as described above. In the MRI apparatus according to the present invention, a combination of at least three types of sub-coils is used as the receiver coil, including a solenoid coil placed around the outer circumference of the subject, and two types of surface coils that are placed on the outer surface of the subject. Since the static magnetic field generated by the MRI apparatus of the present invention is directed vertically, these three types of sub-coils are configured in such a manner that a magnetic field directing orthogonal to the static magnetic field is generated or detected. In addition, these sub-coils are configured to have a geometric arrangement that is free from magnetic coupling between the coils, or the magnetic coupling is removable by a publicly known decoupling means, and with this arrangement, it is possible to obtain a g-factor that is favorable in any of the directions x, y, and Z.

A first embodiment of the receiver coil including such sub-coils as described above is shown in FIG. 2. The receiver coil being illustrated is made up of; a first coil 3-1 forming a current loop in the plane parallel to the z-axis, second coils 5-1 and 5-2 each forming two current loops in the plane intersecting the plane of the current loop of the first coil, and third coils 7-1 and 7-2 that are placed on the positions approximately overlapping the second coils 5-1 and 5-2 in the z-axial direction, each forming three current loops on the plane intersecting the plane of the current loop of the first coil. In the figure, only one block is shown that is made up of one first coil 3-1, a pair of the second coils, and a pair of third coils. However, according to a purpose of imaging and a method of imaging, multiple blocks that are combined in the body axis direction of the subject may be used as the receiver coil.

Figure 3:
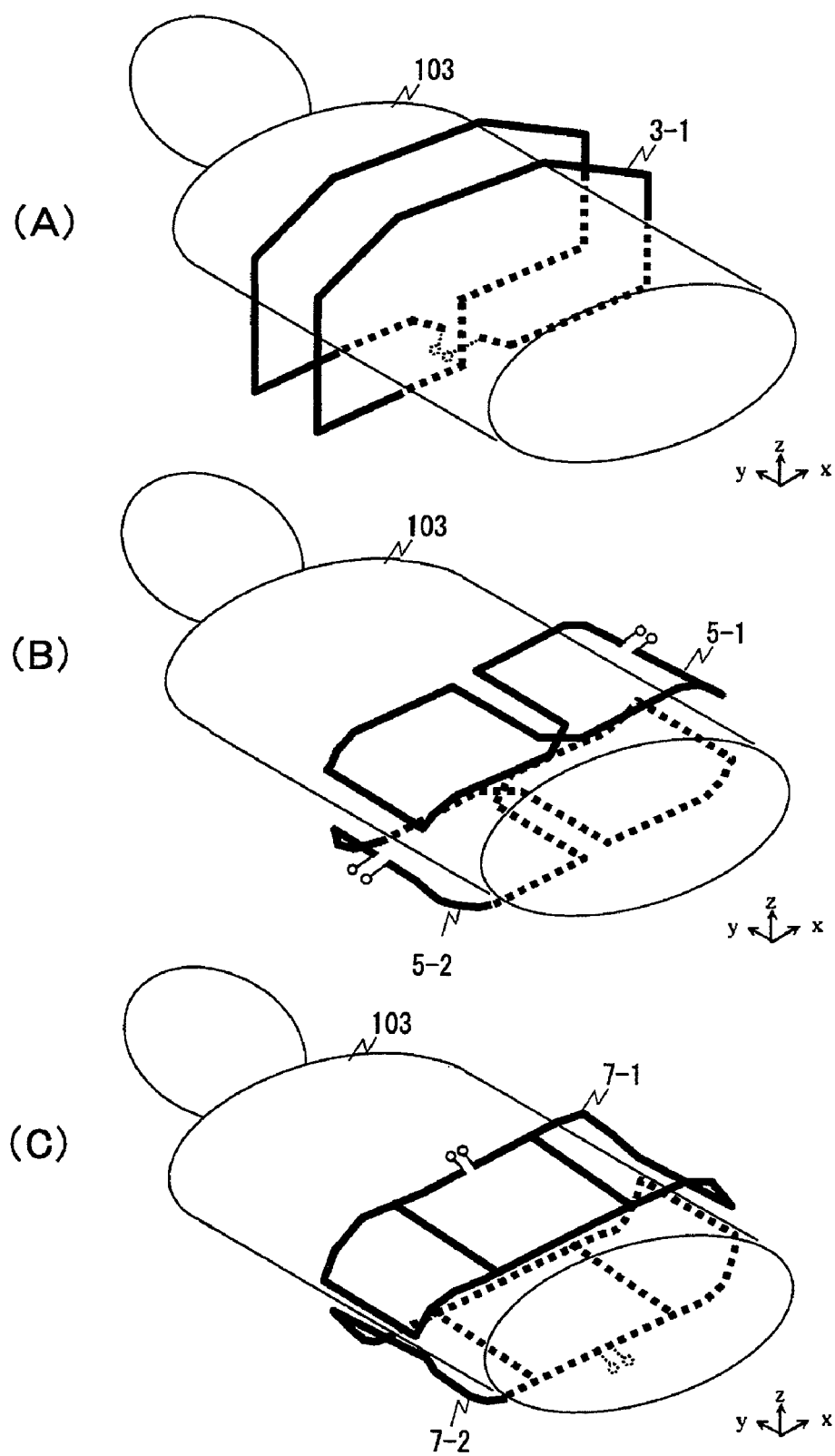
FIG. 3 illustrates sub-coils constituting the receiver coil as shown in FIG. 2, and (A) illustrates a first coil, (B) illustrates a second coil, and (C) illustrates a third coil.
Figure 4:
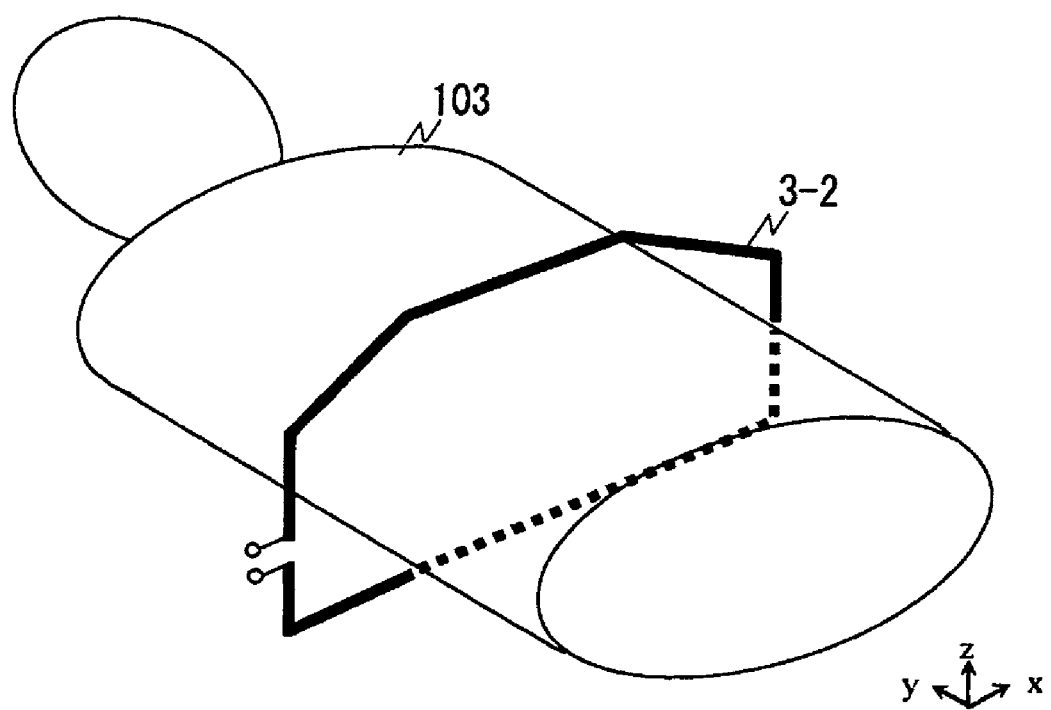
FIG. 4 illustrates a modified example of the first coil.

As shown in FIG. 3(A), the first coil 301 is a solenoid coil made up of a pair of loop coils. The current loops formed respectively by the loop coils are placed in parallel with the plane including an axis in the z-direction (xz plane), and the two loop coils arranged in such a manner as surrounding the outer circumference of the subject 103 with a space in the body axis direction (y-direction) of the subject. A direction of the magnetic field generated by the solenoid 3-1 (a direction of the magnetic field detected by the solenoid coil) corresponds to the y-direction. Though not illustrated, the solenoid coil 3-1 is used in such a manner that a coil conductor is partitioned at multiple portions by a capacitor, and the resonance frequency of the coil is subjected to matching with the nuclear magnetic resonance frequency. It is to be noted here that other than the coil as shown in FIG. 3(A), one-turn solenoid coil 3-2 as shown in FIG. 4 may be employed as the first coil 3-1.

As shown in FIG. 3(B), the second coils 5-1 and 5-2 are butterfly coils each having two current loops, and the two current loops intersect the plane (xz plane) of the current loop of the first coil 3-1, and arranged in the direction orthogonal to the z-direction (here, lateral direction of the subject: x-direction). The direction of the magnetic field generated by the second coils 5-1 and 5-2 as described above is x-direction or z-direction, and it is orthogonal to the direction of the magnetic field generated by the first coil 3-1 (y-direction). Therefore, electromagnetic coupling therebetween is weak. It is to be noted that only either one of the second coils 5-1 and 5-2 may be employed. However, in the present embodiment, two butterfly coils are arranged in such a manner as opposed to each other placing the subject 103 therebetween. In general, the two coils opposed to each other in position as described above may establish an electromagnetic coupling. However, in the present embodiment, such magnetic coupling is suppressed by using, for instance, an amplifier of low-input impedance for signal detection. If the distance between the butterfly coils 5-1 and 5-2 is short relative to the size of the two current loops respectively held by the butterfly coils 5-1 and 5-2, the magnetic coupling cannot be sufficiently suppressed even though the aforementioned method is employed. Therefore, another suppressing means is required. This suppression of the magnetic coupling between the upper and the lower coils will be described in detail later.

As shown in FIG. 3(C), the third coils 7-1 and 7-2 are coils having three current loops, and these three current loops are arranged in the x-direction, intersecting the current loop plane (xz plane) of the first coil 3-1, similar to the two current loops of the second coil. Therefore, the electromagnetic coupling between the third coil and the first coil is also weak. It is to be noted that only either one of the third coils 7-1 and 7-2 may be employed. However, in the present embodiment, those two coils are arranged in such a manner as opposed to each other placing the subject 103 therebetween, and according to a publicly known method, for instance, by using an amplifier with low input impedance for signal detection, the magnetic coupling is suppressed.

Figure 5:
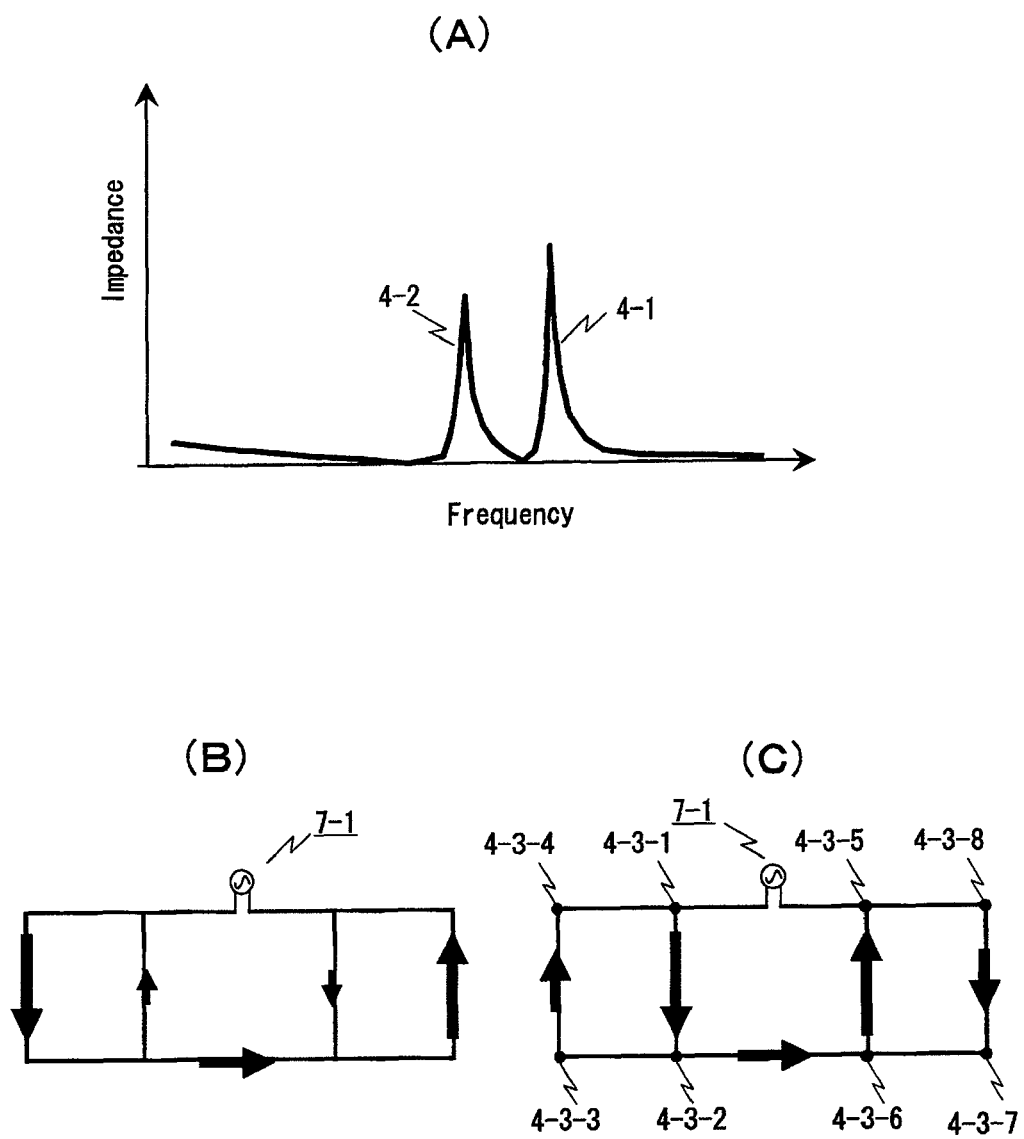
FIG. 5 includes diagrams to explain an operation mode of the third coil.

As shown in FIG. 5(A), two resonance modes 4-1 and 4-2 exist in the third coil 7-1 (7-2). FIG. 5(B) and FIG. 5(C) illustrate current distributions of these resonance modes, respectively, represented by the thickness of arrow. The resonance mode 4-2 having a lower resonance frequency as shown in FIG. 5(B) does not form a current loop on the central conductor loop. As for the resonance mode 4-1 having a higher resonance frequency as shown in FIG. 5(C), the first to the third current loops are formed: a conductor path joining node 4-3-4, node 4-3-1, node 4-3-2, and node 4-3-3; a conductor path joining node 4-3-1, node 4-3-2, node 4-3-6, and node 4-3-5; and a conductor path joining node 4-3-5, node 4-3-8, node 4-3-7, node 4-3-6. In the present invention, the resonance frequency is used in the resonance mode 4-1, which is higher. A condenser (not illustrated), inserted in the third coil 7-1 (7-2) and the like are adjusted in accordance with the resonance frequency, thereby operating the coil 7-1 (7-2) in the resonance mode 4-1.

Figure 6:
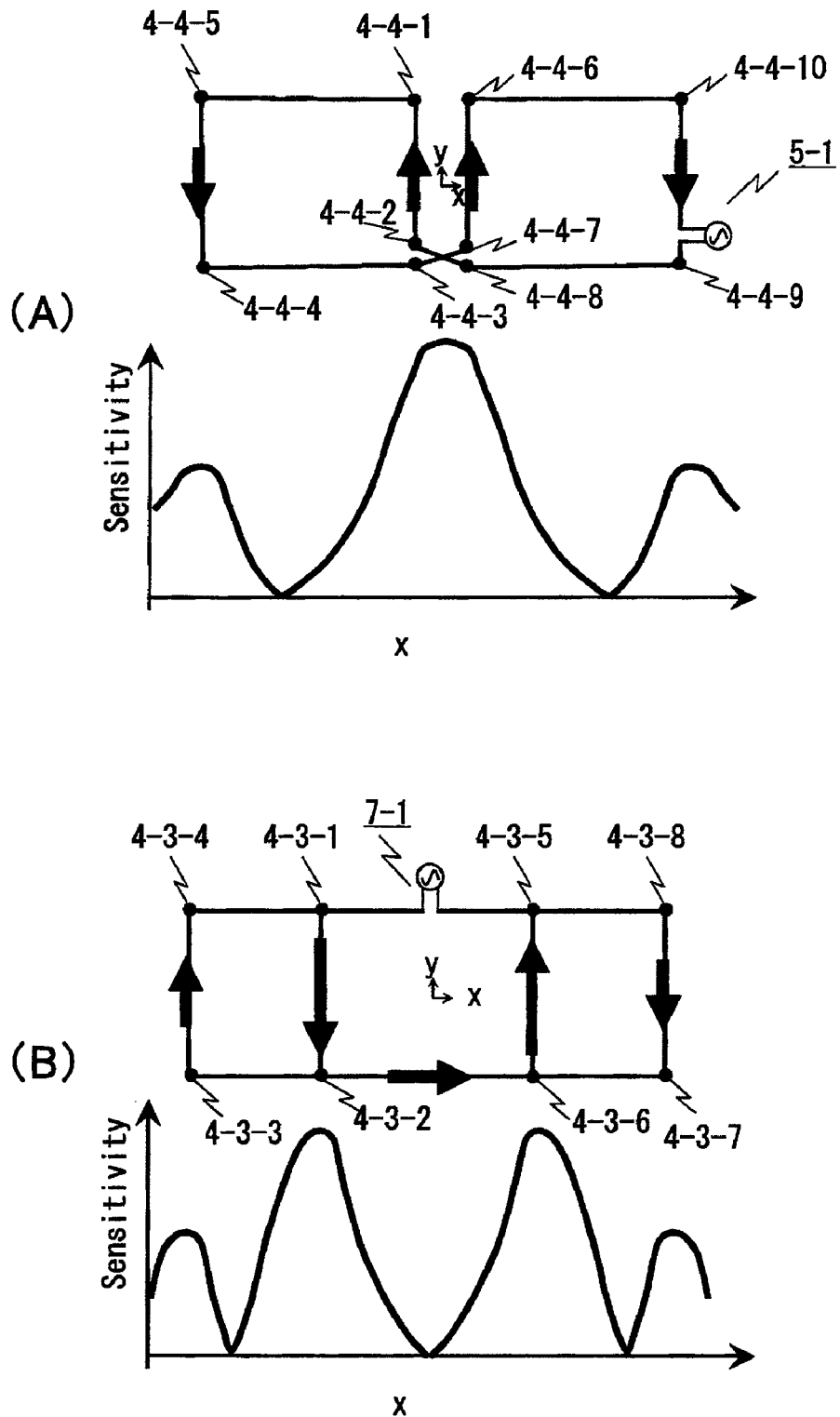
FIG. 6 includes diagrams to explain the arrangements of the second coil and the third coil.

Next, an explanation will be made regarding the arrangement of the second coils 5-1 and 5-2 which form the aforementioned two current loops, and the third coils 7-1 and 7-2 which form the three current loops. In the coil having multiple current loops being formed, a sensitivity distribution in the array direction of the current loops is the highest near the coil conductor. Therefore, as shown in FIG. 6(A), there exist three high sensitivity portions and low sensitivity portions therebetween in the sensitivity distribution of the second coil 5-1 forming the two current loops. In the sensitivity distribution of the third coil 7-1 forming the three current loops, as shown in FIG. 6(B), there exist four high sensitivity portions and low sensitivity portions therebetween. In the present embodiment, these two types of coils having the sensitivity distributions as described above are arranged in such a manner that the maximum sensitivity portions of one coil are superimposed almost over the minimum sensitivity portions of the other coil.

In other words, the coil conductor joining the node 4-3-1 and the node 4-3-2 of the third coil 7-1 is positioned between the coil conductor joining the node 4-4-5 and the node 4-4-4, and the coil conductor joining the node 4-4-1 and the node 4-4-2 of the second coil 501. The coil conductor joining the node 4-3-5 and the node 4-3-6 of the third coil 701 is positioned between the coil conductor joining the node 4-4-6 and the node 4-4-7 and the coil conductor joining the node 4-4-10 and the node 4-4-9 of the second coil 5-1. As thus described, the second and the third coils are superimposed on one another in such a manner that the portions having the maximum sensitivity are alternately arranged, being positioned symmetrically with respect to y-axis, thereby minimizing the electromagnetic coupling between the second coil and the third coil.

Figure 7:
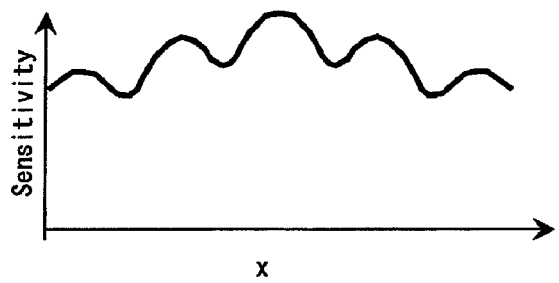
FIG. 7 is a chart showing a combined sensitivity distribution of the second coil and the third coil.

FIG. 7 shows a combined sensitivity distribution of these two types of coils. It is found that in the combined sensitivity, there is no area where the sensitivity is zero, within the region where the subject exists. When the second coil and the third coil are superimposed on one another as thus described, it is difficult to perfectly match the two areas having the maximum sensitivity of the third coil, to the two areas having the minimum sensitivity of the second coil, due to a restriction of producing accuracy. However, it is preferable to achieve a match therebetween even with a displacement within 20% length of the x-direction width of the second coil. Even if there is around 20% displacement in the x-direction width of the second coil, due to restrictions in implementation, it is possible to expect an improved effect in g-factor.

Figure 8:
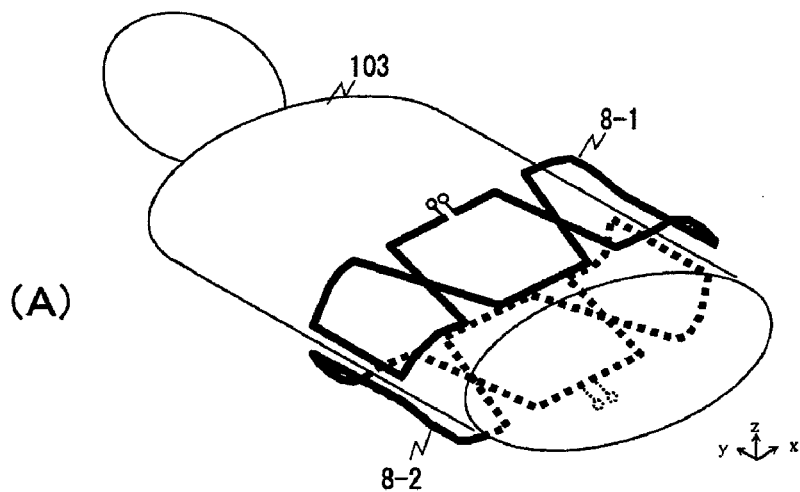
FIG. 8 illustrates a modified example of the third coil.
Figure 8:
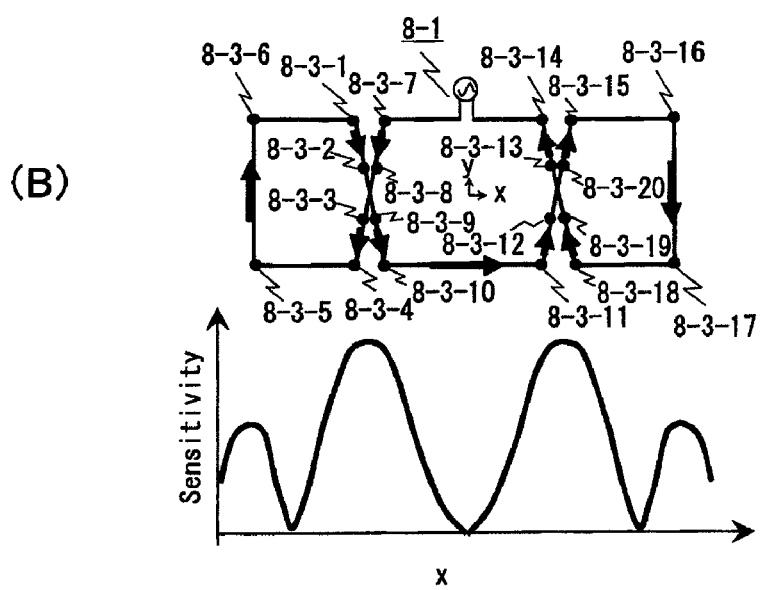

As the third coil of the present embodiment, any coil that forms three adjacent current loops may be applicable. In addition to the coil as shown in FIG. 3(C), it is possible to employ the coils 8-1 and 8-2 having a shape of one-turn loop coil twisted at two points, as shown in FIG. 8, for example. FIG. 8(A) is a perspective view showing a relationship between the coils 8-1 and 8-2 and the subject 103. FIG. 8(B) shows a diagram viewing the coil 801 from the z-axis positive direction, and a chart showing the sensitivity distribution in the x-direction.

Figure 27:
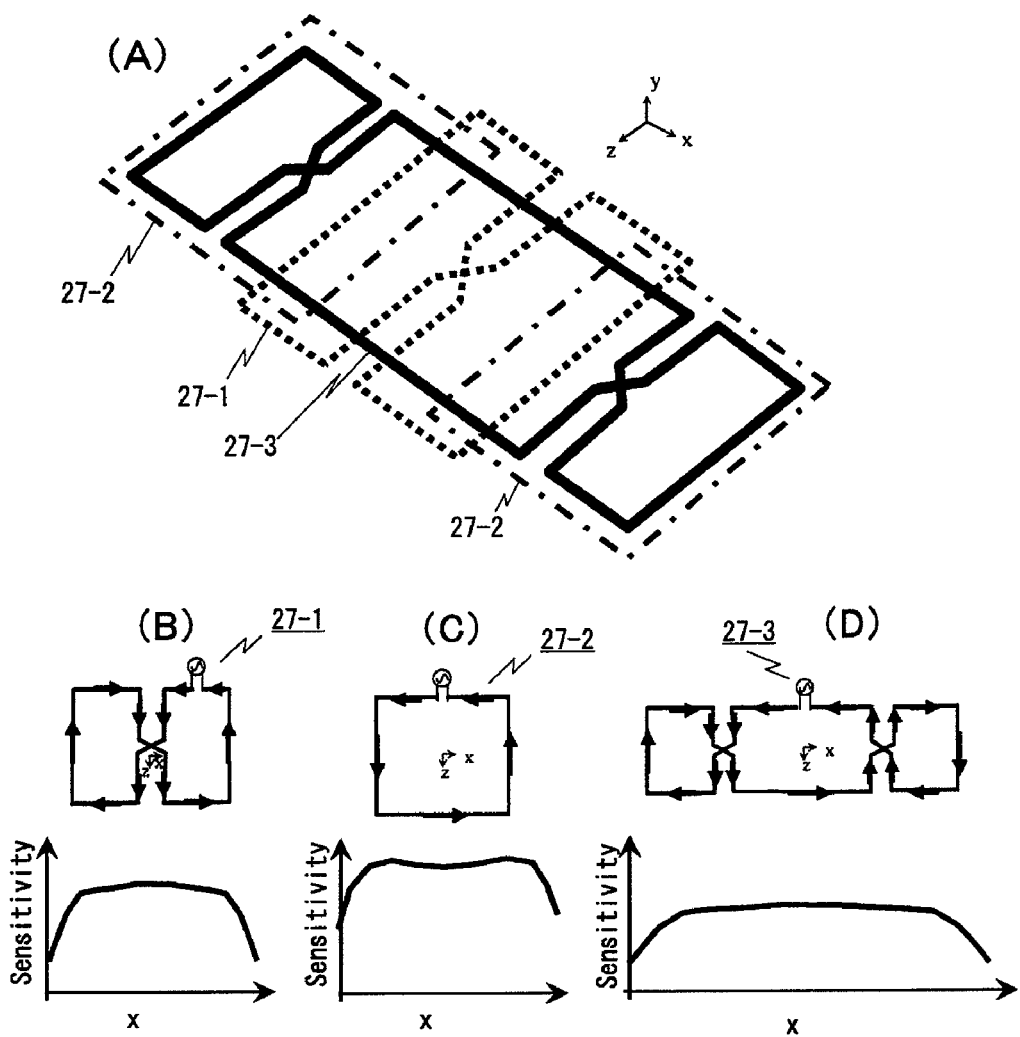
FIG. 27 illustrates arrangement examples of a conventional receiver coil used for the horizontal magnetic field type MRI.
Figure 28:
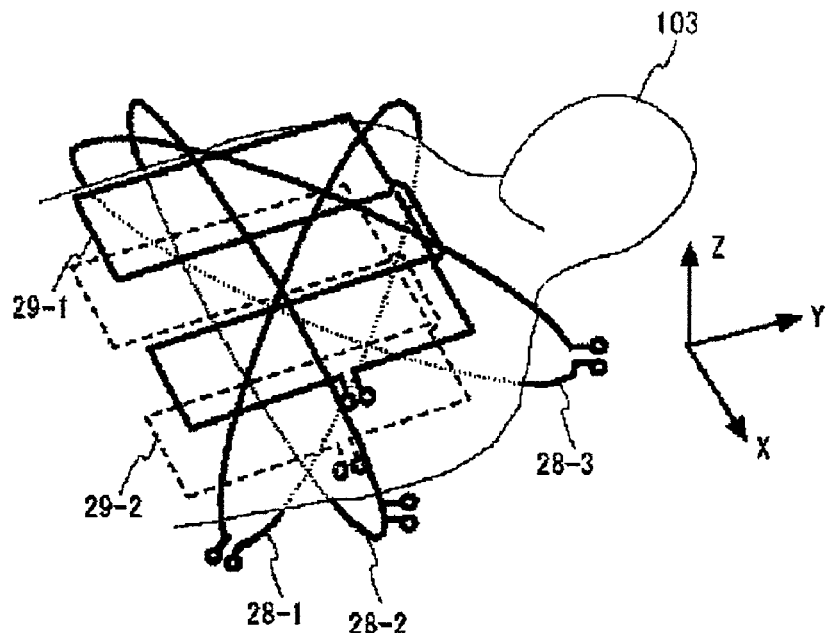
FIG. 28 illustrates arrangement examples of a conventional receiver coil used for a vertical magnetic field type MRI.

In the coil 8-1, the first current loop is formed by a conductor path joining node 8-3-3, node 8-3-4, node 8-3-5, node 8-3-6, node 8-3-1, and node 8-3-2, the second current loop is formed by a conductor path joining node 8-3-9, node 8-3-10, node 8-3-11, node 8-3-12, node 8-3-13, node 8-3-14, node 8-3-7, and node 8-3-8, and the third current loop is formed by a conductor path joining node 8-3-20, node 8-3-15, node 8-3-16, node 8-3-17, node 8-3-18, and node 8-3-19. Unlike the coil 7-1, there is only one resonance mode in the coil 8-1. As for the sensitivity distribution, the sensitivity becomes the maximum, around the conductor joining the nodes 8-3-7, 8-3-8, 8-3-9, and 8-3-4, around the conductor joining the nodes 8-3-1, 8-3-2, 8-3-9, and 8-3-10, around the conductor joining the nodes 8-3-11, 8-3-12, 8-3-20, and 8-3-15, and around the conductor joining the nodes 8-3-18, 8-3-19, 8-3-13, and 8-3-14. As explained above, since the receiver coil detects an RF magnetic field in the direction orthogonal to the static magnetic field (z-direction), the sensitivity distribution of the coil 8-1 is different from that of the coil used in the horizontal magnetic field use coil, even though the coil 8-1 looks similar to the horizontal magnetic field use coil as shown in FIG. 27(D).

Similar to the case of coil 7-1, the coil 8-1 is also arranged in such a manner that the portions having the maximum sensitivity distribution are approximately superimposed over the portions having the minimum sensitivity distribution of the second coil, thereby configuring a receiver coil that suppresses magnetic coupling between each other.

Next, decoupling will be explained, when more than one block combining the aforementioned first to third coils is arranged in the body axis direction (y-direction) of the subject 103. As described above, the first coil and the second coil, the first coil and the third coil, and the second coil and the third coil are respectively arranged in such a manner that the magnetic coupling is reduced to the minimum. However, if the first to the third coils are arranged in the Y-direction, each more than one, it becomes necessary to suppress the electromagnetic coupling between the coils of the same type. Decoupling between the same type coils will be explained in the following.

Figure 9:
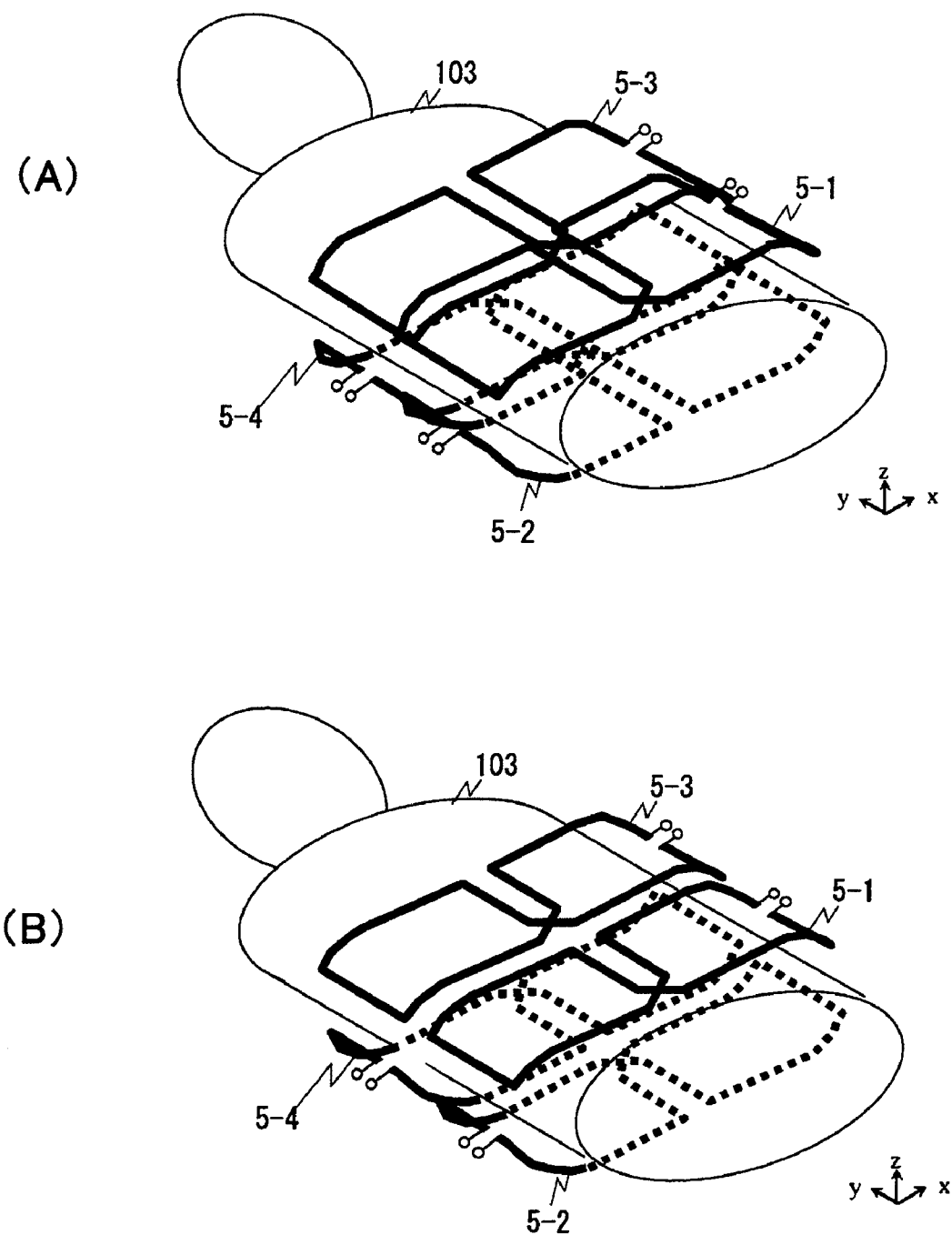
FIG. 9 illustrates a state where more than one second coils are arranged in the y-direction.

FIG. 9(A) and FIG. 9(B) each illustrates a situation where the second coils 5-1 and 5-2, and 5-3 and 5-4 are arranged in the y-direction. In FIG. 9(A), the two coils 5-1 and 5-3, and the coils 5-2 and 5-4, which are arranged on the upper and the lower sides placing the subject 103 therebetween, are respectively overlapped appropriately in the y-direction (e.g., around 10% as a ratio of area), thereby removing the magnetic coupling. Alternatively, as shown in (B), the magnetic coupling can be removed by increasing the distance between the coil 5-1 and the coil 5-3, and between the coil 5-2 and the coil 5-4 in the y-direction. In this case, while the distance between the coils is increased, an amplifier with low input impedance is used for signal detection, thereby suppressing the magnetic coupling. Increasing the distance between the coils as described above allows a reduction of area of the current loop, compared to the case where the coils are arranged in such a manner as being overlapped. Therefore, as far as the distance between the upper coils and the lower coils is the same, electromagnetic coupling between the coils vertically opposed is reduced, and it is possible to enhance an effect by suppressing the magnetic coupling, utilizing the amplifier with low input impedance.

Figure 10:
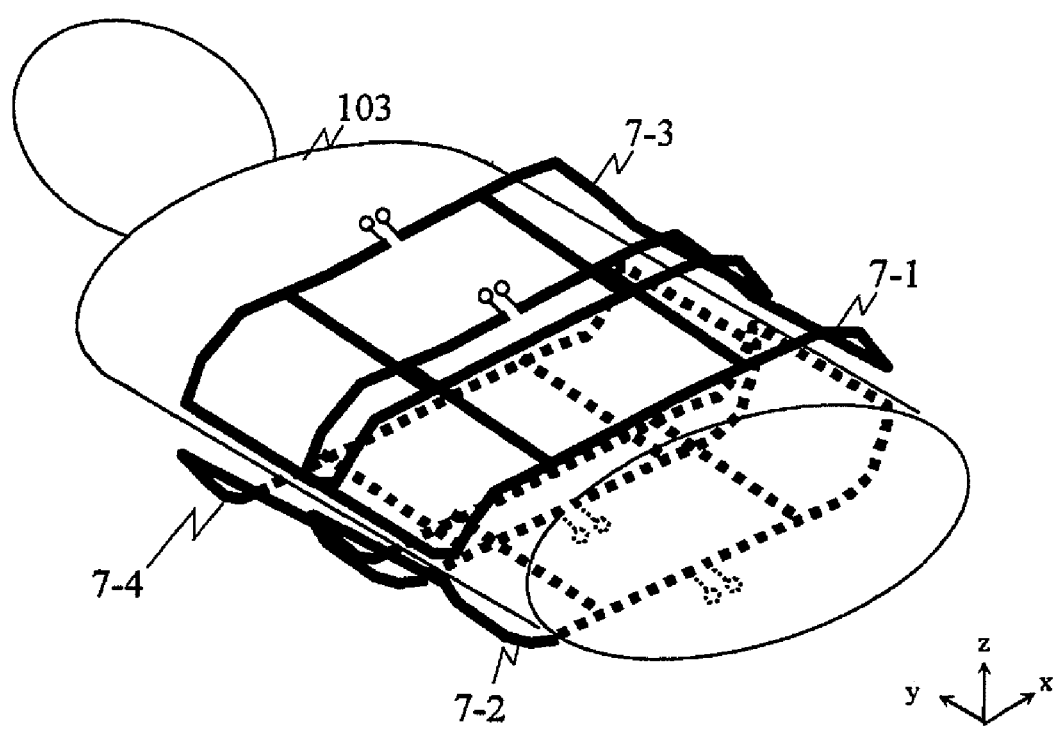
FIG. 10 illustrates a state where more than one second third coils are arranged in the y-direction.

FIG. 10 illustrates a state where the third coils 7-1 and 7-2, and 7-3 and 7-4 are arranged in the y-direction. Also in the third coils, it is possible to suppress the magnetic coupling between the adjacent coils, by placing the coils adjacent in the y-direction in such a manner as being overlapped appropriately. Similar to the case of the second coils, it is further possible to suppress the magnetic coupling by increasing a distance between the adjacent coils, though this situation is not illustrated.

As thus described, the second coils and the third coils can be placed continuously side by side in the y-direction. However, if the solenoid coil 3-1 or 3-2 being the first coil is placed side by side in the y-direction, there may be generated an extremely large electromagnetic coupling therebetween. Therefore, even though a decoupling method using the amplifier with low impedance is employed for outputting, it is not possible to sufficiently suppress the magnetic coupling. However, in imaging a wide field such as whole body imaging, it is general to pick up images by partitioning an imaging area into multiple measuring blocks in the body axis direction (in the y-direction of the vertical magnetic field MRI) of the subject. Therefore, in the present embodiment, it is configured such that one solenoid exists in one measuring block, and a solenoid other than the one existing in the measuring block that is in the course of picking up an image (a solenoid not used for imaging) is not allowed to operate.

Figure 11:
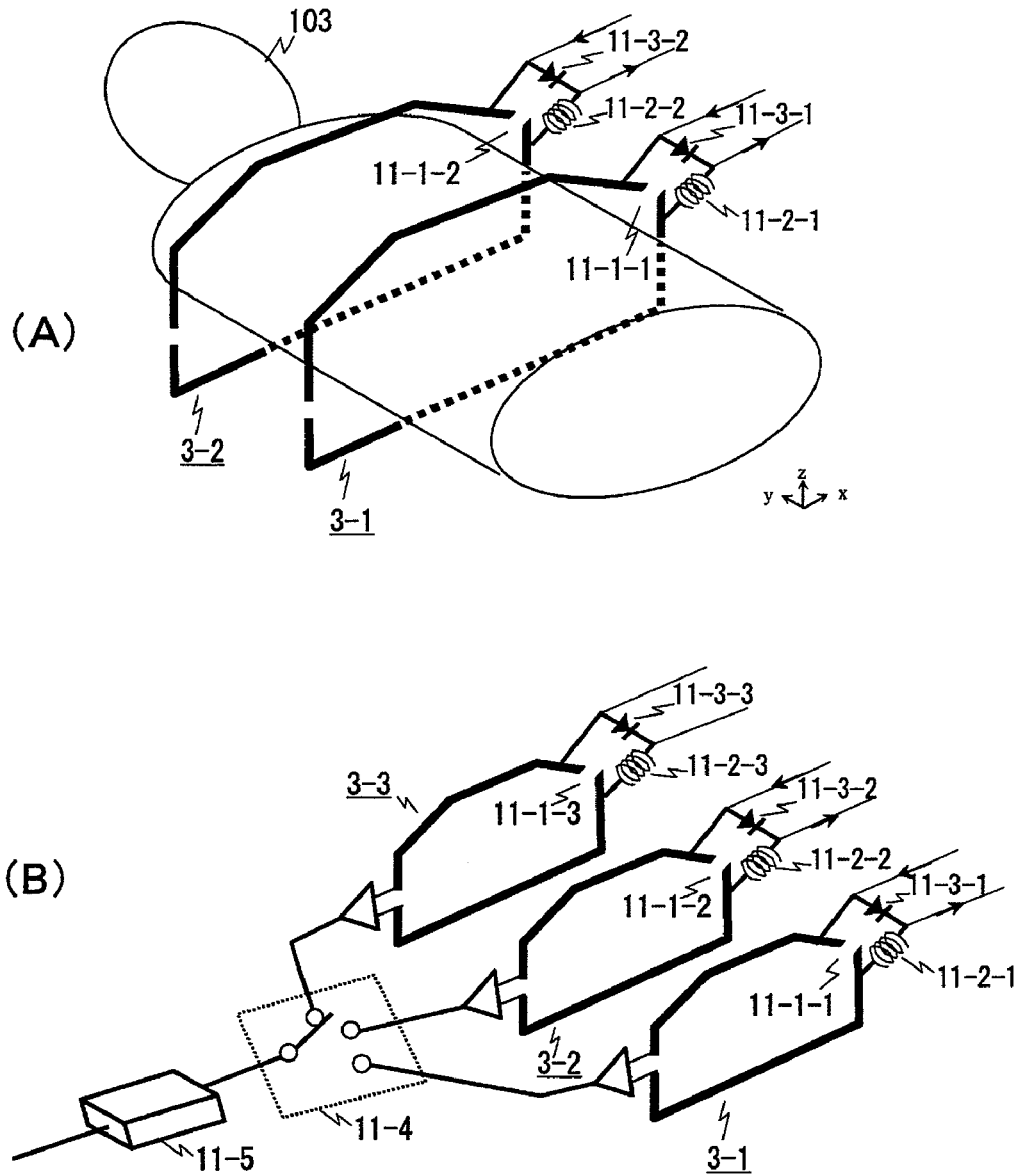
FIG. 11 shows a configuration of the receiver coil in the case where more than one first coils is arranged in the y-direction.

FIG. 11 shows a configuration in which more than one solenoid coils 3-1, 3-2, and 3-3 arranged in the y-direction are selectively operated. As shown in FIG. 11(A), an inductance 11-2 is inserted in parallel with a capacitor 11-1 that is connected in series with a part of each of the solenoid coils 3-1 to 3-3. The inductance is set to have a value that shows a resonance peak in the nuclear magnetic resonance frequency, and the inductance 11-2 and the capacitor 11-1 form a resonance circuit. In this resonance circuit, a diode 11-3 is inserted that is turned ON and OFF according to a control signal from the sequencer 104, for instance. In addition, more than one solenoid coils are connected to one receiver 11-5 via a switch 11-4.

In the configuration as described above, when the diode 11-3 is turned ON, resonance occurs between the inductor 11-2 and the capacitor 11-1, and high impedance is generated. Therefore, this situation is equivalent to a case where a large resistance is inserted in the capacitor 11-1 part. Thus a flow of the loop current is blocked, and the operation as an RF coil does not word. By way of example, if the imaging is performed in the measuring block where the coil 3-3 exists, as shown in FIG. 11(B), DC electricity is allowed to flow in the diodes 11-3-2 and 11-3-1, and not allowed to flow in the diode 11-3-3. At the same time, changeover of the switch 11-4 is performed, and an output cable of the coil 3-3 is connected to the receiver 11-5. Accordingly, only the coil 3-3 operates as the solenoid coil, and the coils 3-1 and 3-2 do not work as the RF coils. In addition, with this configuration, signals from multiple first coils can be processed by one receiver 11-5 (a receiver prepared for the first coil).

As discussed above, the receiver coil of the present embodiment is arranged so that no magnetic coupling is generated, or the magnetic coupling is minimized, between coils different in type, or between coils of the same type. Therefore, this receiver coil is suitable not only for general imaging, but also for the imaging time shortening technique (parallel imaging) in which the phase encoding step is made wider and the FOV is made smaller.

Compared to a general phase encoding step, the number of phase encoding being measured is smaller and the steps are wider in the aforementioned imaging time shortening technique. Signals detected in each of the sub-coils of the receiver coil are subjected to sampling in the receivers, 108-1 to 108-n respectively connected to the sub-coils, and then, reconstructed to an image data and thereafter synthesized, so as to form an image of the area that the entire receiver coil covers. Alternatively, before reconstructing into the image data, synthesizing is performed and it is followed by reconstruction. When the signals are synthesized, aliasing generated in the image is removed by using the sensitivity distribution information of each sub-coils of the receiver coil. A calculation for removing the aliasing in the imaging time shortening technique is described in the non-patent document 1, for instance. As for a noise level in this calculation for removing aliasing artifact, g-factor may be a problem, since the g-factor is dependent on the geometric arrangement of the sub-coils that constitute the receiver coil. In the present embodiment, coils are arranged so that overlapping of the sensitivity distributions of three types of coils is minimized and also the electromagnetic coupling among them is removed. Therefore, the g-factor can be made smaller (e.g., two or less) and it is possible to obtain an MR image that is high in SNR, and high in quality.

In addition, in order to effectively perform the aliasing removal processing in the imaging time shortening technique, g-factor in the phase encoding direction is significant. In the present embodiment, the sub-coils have a configuration of arrangement so that sensitivity distributions are respectively different in all the directions x, y, and z. Therefore, even any one of the directions is selected as the phase encoding direction, the imaging time shortening technique is available.

Figure 12:
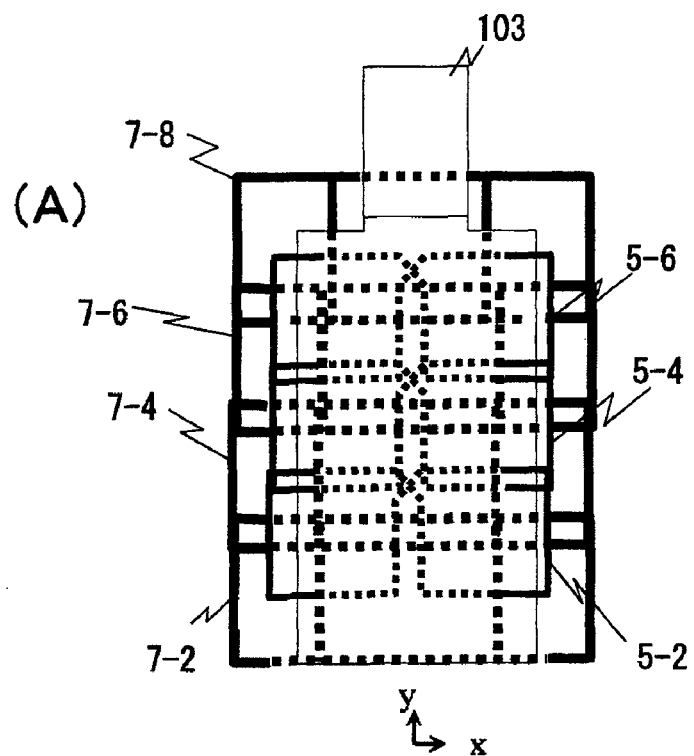
FIG. 12 illustrates a second embodiment of the present invention, (A) illustrates a coil arrangement on the chest side of the subject, and (B) illustrates a coil arrangement on the backside.
Figure 12:
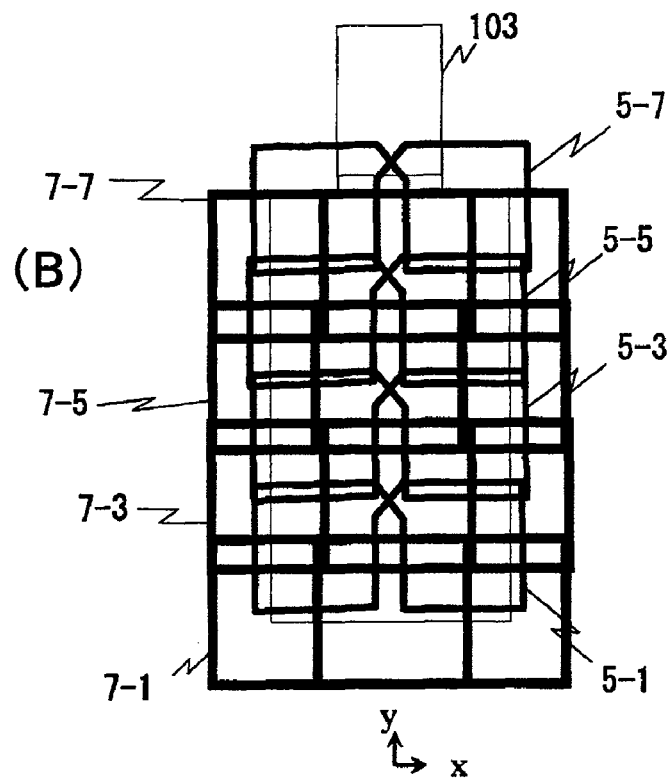

Next, another embodiment of the receiver coil in the MRI apparatus according to the present invention will be explained. FIG. 12 and FIG. 13(A) illustrate the second embodiment of the receiver coil. It is to be noted here that in the figures, only the second and the third coils are shown and the first coil is omitted. However, similar to the first embodiment, a sub-coil which is placed around the outer circumference of the subject and produces a current loop in a plane parallel to an axis in the z-direction is used as the first coil.

In the present embodiment, the second and the third coils are arranged on the upper side and lower side (chest side and backside) placing the subject therebetween, similar to the first embodiment. However, the present embodiment features that the upper and the lower coils are displaced from each other in the body axis direction of the subject 103 (a direction orthogonal to an array direction of the current loop: y-direction). Both of FIGS. 12 (A) and (B) are illustrations viewed from the chest side of the subject 103. FIG. 12(A) illustrates the second coils 5-2, 5-4, and 5-6, and the third coils 7-2, 7-4, 7-6, and 7-8, which are arranged on the backside. FIG. 12(B) illustrates the second coils 5-1, 5-3, 5-5, and 5-7, and the third coils 7-1, 7-3, 7-5, and 7-7, which are arranged on the chest side. FIG. 13(A) is an illustration of the second coil arrangement viewed from the lateral side of the subject.

As illustrated, in the present embodiment, coils of the same type are arranged in such a manner that the upper coils and the lower coils are displaced by half cycle (i.e., the current loops are displaced from each other by half-length of the loop). With the arrangement as described above, electromagnetic coupling between the chest-side coils and the backside coils is made smaller, compared to the case where the coils of the same type are arranged in such a manner as directly opposed to each other as shown in FIG. 13(B). Accordingly, it is possible to enhance a suppression effect by the magnetic coupling suppressing method that employs the amplifier with low impedance for outputting. Therefore, this arrangement according to the present embodiment is effective, when the distance between the upper and the lower coils is short relative to the sizes of the two current loops held by each coil, and therefore it is not possible to sufficiently suppress the magnetic coupling even if the amplifier with low impedance is used for outputting. Furthermore, the distance between the chest-side coil and the backside coil can be set shorter, thereby increasing a degree of freedom in designing a coil that is suitable for the subject figure.

Figure 13:
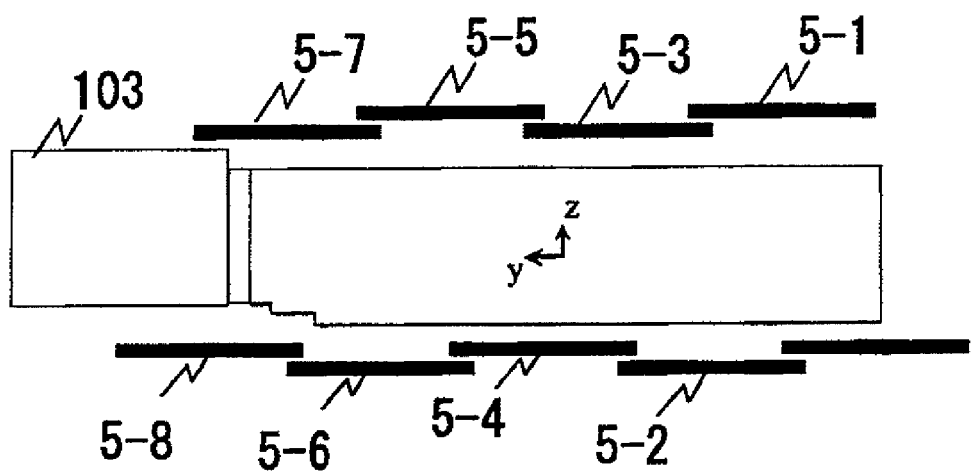
FIG. 13 illustrates an arrangement of coils of the same type on the upper and lower sides, (A) illustrates the second embodiment, and (B) illustrates a coil arrangement different from (A)
Figure 13:
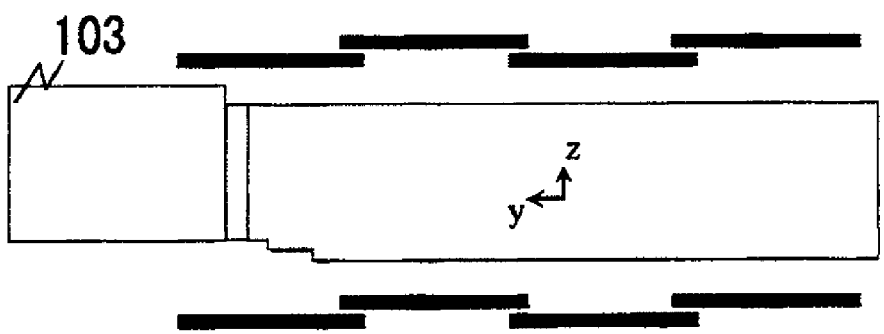

It is to be noted that in FIG. 12 and FIG. 13, an example where the coil used as the third coil is of the type as shown in FIG. 3(C). However, also in the present embodiment, a coil having a shape being twisted as shown in FIG. 8 may be available as the third coil. In addition, in order to suppress the magnetic coupling between the coils of the same type with respect to the y-direction, here has been shown an example where coils of the same type are arranged in such a manner as being overlapped in the y-direction. However, it is further possible to arrange the coils in such a manner as placing a distance between the coils as shown in FIG. 9(B).

Figure 14:
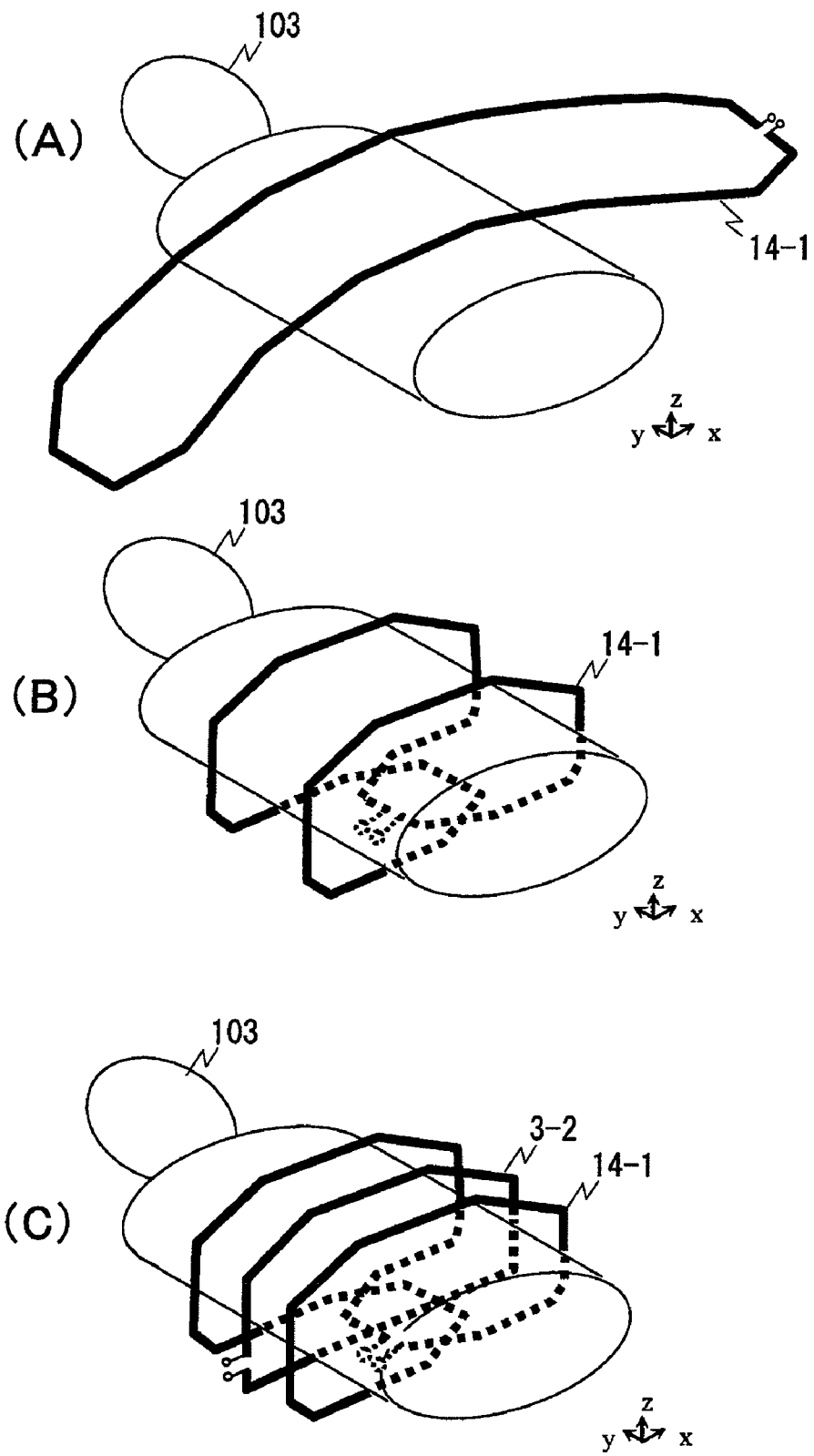
FIG. 14 illustrates a third embodiment of the present invention.

FIG. 14 illustrates the third embodiment of the present invention. In the present embodiment, the fourth coil is employed in addition to the first to the third coils. In the figure, the second and the third coils are omitted, but the configuration thereof is the same as the first and the second embodiments.

Any coil can be used as the fourth coil, if the coil has no substantial magnetic coupling with the first to the third coils, or if the magnetic coupling therebetween can be suppressed by the publicly known decoupling method. In the embodiment as shown in FIG. 14, one-turn solenoid coil 3-2 as shown in FIG. 4 is employed as the first coil, and together with this solenoid coil, a sub-coil 14-1 is used, which is arranged around the outer circumference of the subject 103.

Figure 15:
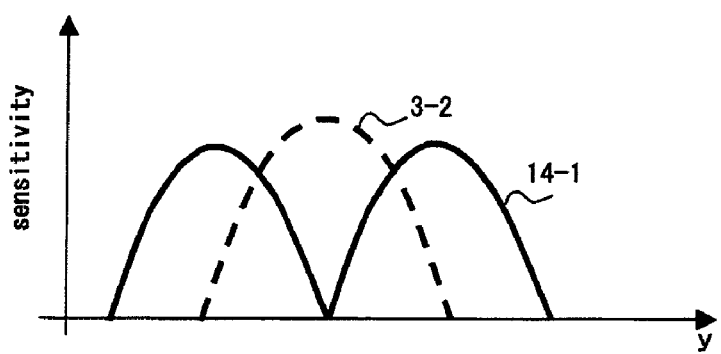
FIG. 15 is a chart showing a sensitivity distribution of the third embodiment.

The fourth coil 14-1 has a structure such that a loop coil being long in the x-direction as shown in FIG. 14(A) is wound around the outer circumference of the subject as shown in FIG. 14(B). FIG. 15 shows sensitivity distributions in the y-direction of the coil 14-1 and the first coil 3-2. As is shown, the coil 14-1 has the maximum sensitivity portions near the conductor that forms two current loops, and has a low sensitivity portion therebetween. Both coils are arranged in such a manner that the low sensitivity portion coincides with the maximum sensitivity portion of the first coil, thereby eliminating the magnetic coupling. Similar to the first coil, the fourth coil does not have any magnetic coupling with the second and third coils. According to the present embodiment, the g-factor can be improved more, by adding the fourth coil.

Figure 16:
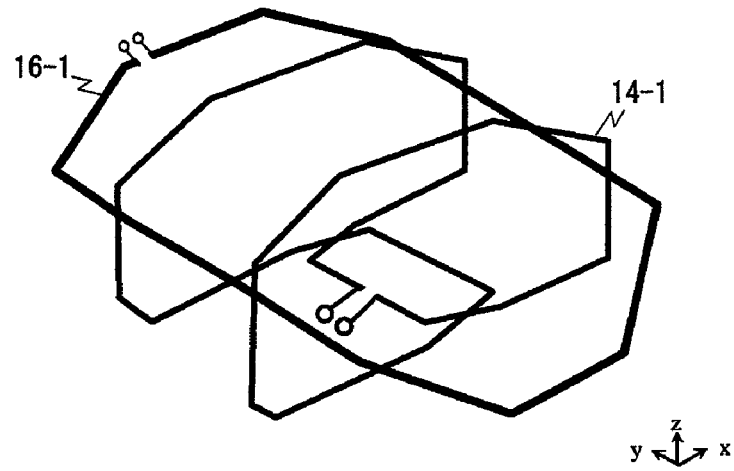
FIG. 16 illustrates modified examples of the third embodiment.
Figure 16:
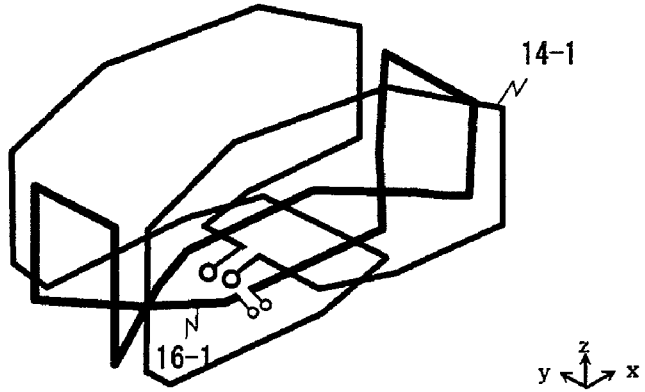

FIG. 16 illustrates an embodiment in which a coil 16-1 of the same type is arranged orthogonal to the fourth coil as shown in FIG. 14. In this illustration, the first to the third coils are omitted, but the configuration thereof is the same as the aforementioned embodiments.

Figure 17:
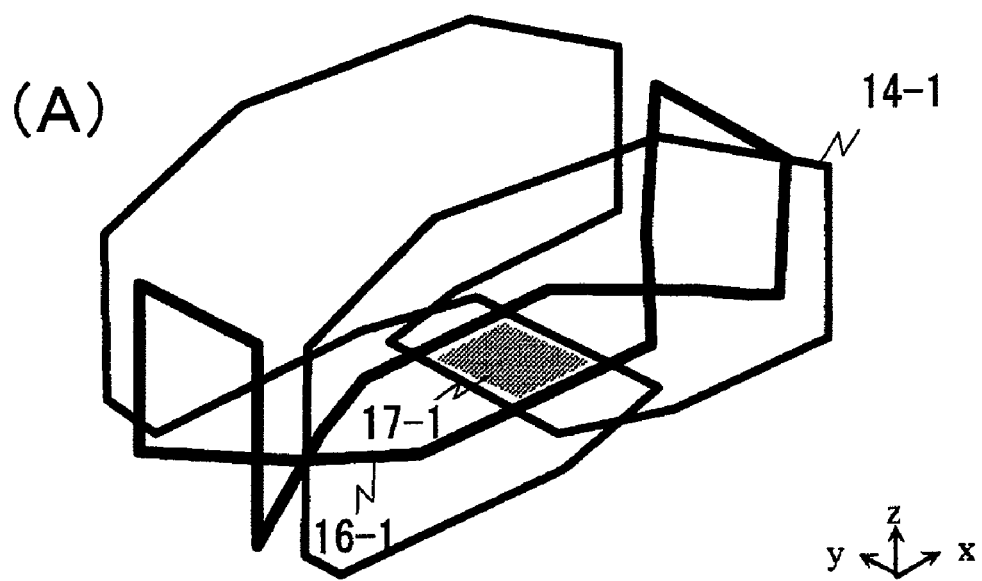
FIG. 17 includes illustrations to explain decoupling in the examples shown in FIG. 16.
Figure 17:
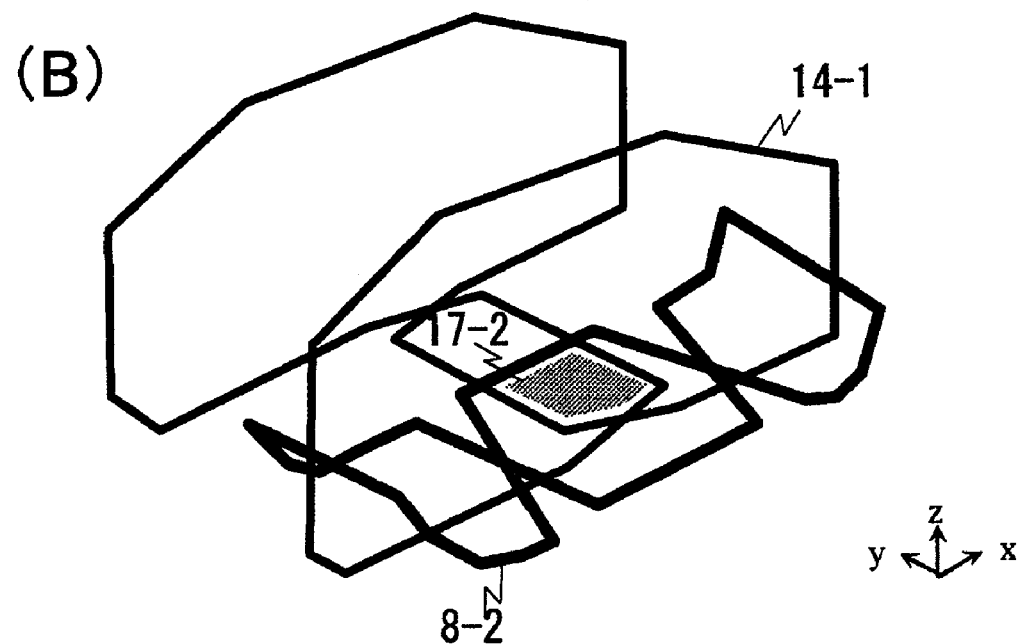

The coil 16-1 has a structure that a loop coil as shown in (A), which is long in the y-direction, is wound around the subject 103. Generally, the electromagnetic coupling between the coil 14-1 and the coil 16-1 is intensive, and such magnetic coupling cannot be sufficiently suppressed even if a low impedance amplifier is used for outputting from both coils. In this case, as shown in FIG. 17(A), the area of the overlapping portion 17-1 between the two coils is adjusted, and thereby the magnetic coupling between both is removed.

The coil 16-1 has no magnetic coupling with the first and the second coils, but if the twisted type coil 8-1 having three current loops as shown in FIG. 8 is employed as the third coil, its shape is similar to the coil 16-1. Therefore, if those coils are arranged as shown in FIG. 17(B), there is an electromagnetic coupling. Also in this case, the electromagnetic coupling can be reduced by adjusting the area of the overlapping portion 17-2. In addition, by the use of the low impedance amplifier, the magnetic coupling can be suppressed, and then, the electromagnetic coupling therebetween can be reduced to a level causing no problem in practical use. Also in the present embodiment, by using an appropriate electromagnetic coupling reducing means with the coil 16-1, the coil 14-1 can be added as a coil of the fourth type, and the g-factor can be improved ever more.

In the explanation above, a butterfly coil having two adjacent current loops is exemplified as the second coil, and a coil having three adjacent current loops is exemplified as the third coil. However, the number of current loops arranged on the surface of the subject is not limited to these examples, and the present embodiment may be sufficiently applicable if one coil has odd-numbered loops and the other coil has even-numbered loops.

Figure 18:
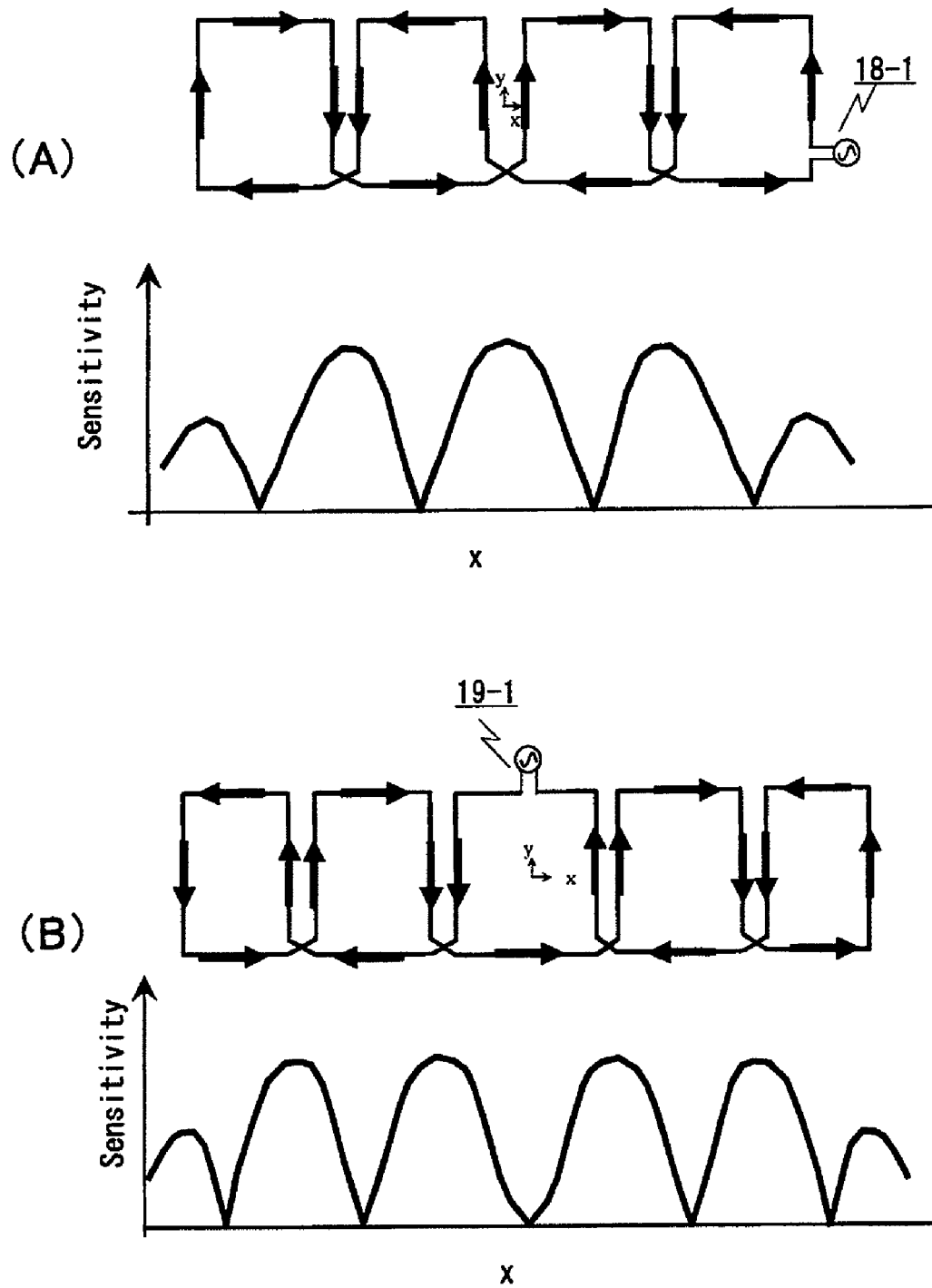
FIG. 18 illustrates a fourth embodiment of the present invention.

By way of example, as shown in FIG. 18(A), the coil 18-1 having four current loops may be used instead of the second coil having two current loops, to be combined with the third coil having three current loops. Alternatively, the coil 18-1 is used as the second coil and coil 19-1 having five current loops as shown in FIG. 18(B) may be used instead of the third coil having three current loops. FIGS. 18(A) and (B) illustrate the sensitivity distributions in the x-direction of the coil 18-1 and 19-1 respectively. The coils 18-1 and 19-1 having those sensitivity distributions are arranged in such a manner that areas of the four points showing the maximum sensitivity of the third coil 19-1 approximately match the areas around the four points showing the minimum sensitivity of the second coil 18-1.

Figure 19:
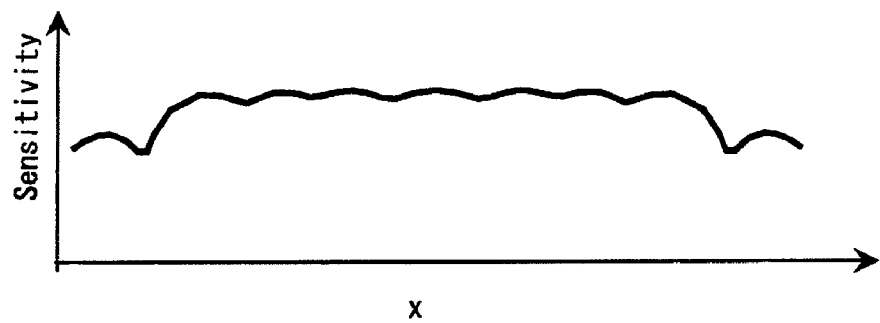
FIG. 19 is a chart showing a combined sensitivity distribution of the second and the third coils in the fourth embodiment.

A sensitivity distribution combining those of the two coils is shown in FIG. 19. It is seen that in the combined sensitivity, there is no area where the sensitivity is zero in the region where the subject exists. Moreover, this combined sensitivity distribution shows a high uniformity, compared to the combined sensitivity distribution (FIG. 7) in the case where a coil having two current loops is used as the second coil, and a coil having three current loops is used as the third coil. Such high uniformity of the combined sensitivity may produce an effect that unevenness in sensitivity in a produced image of the subject is reduced. Two types of coils having the arrangement as described above are used together with the first coil arranged in a plane including an axis parallel to the static magnetic field, and thereby enabling an imaging with a high depth sensitivity and a high-speed imaging of any section of wide area such as whole body.

Various embodiments of the receiver coil in the MRI apparatus according to the present invention have been explained, with reference to the accompanying drawings. It is to be noted here that the shape of the first to the third sub-coils, the shape and the number of coils of different type being added to these three kinds of coils, and the electromagnetic coupling shortening means may be combined and modified appropriately. By way of example, more than one coil of different type may be added to the three kinds of coils. This may increase the variety of coils and provide a coil arrangement that is able to reduce the g-factor. Another example may be possible such as further dividing the second coil and the third coil into multiple coils in lateral directions. For this case, the number of the coil increases, and this may provide a coil arrangement that is able to reduce the g-factor even more.

Figure 20:
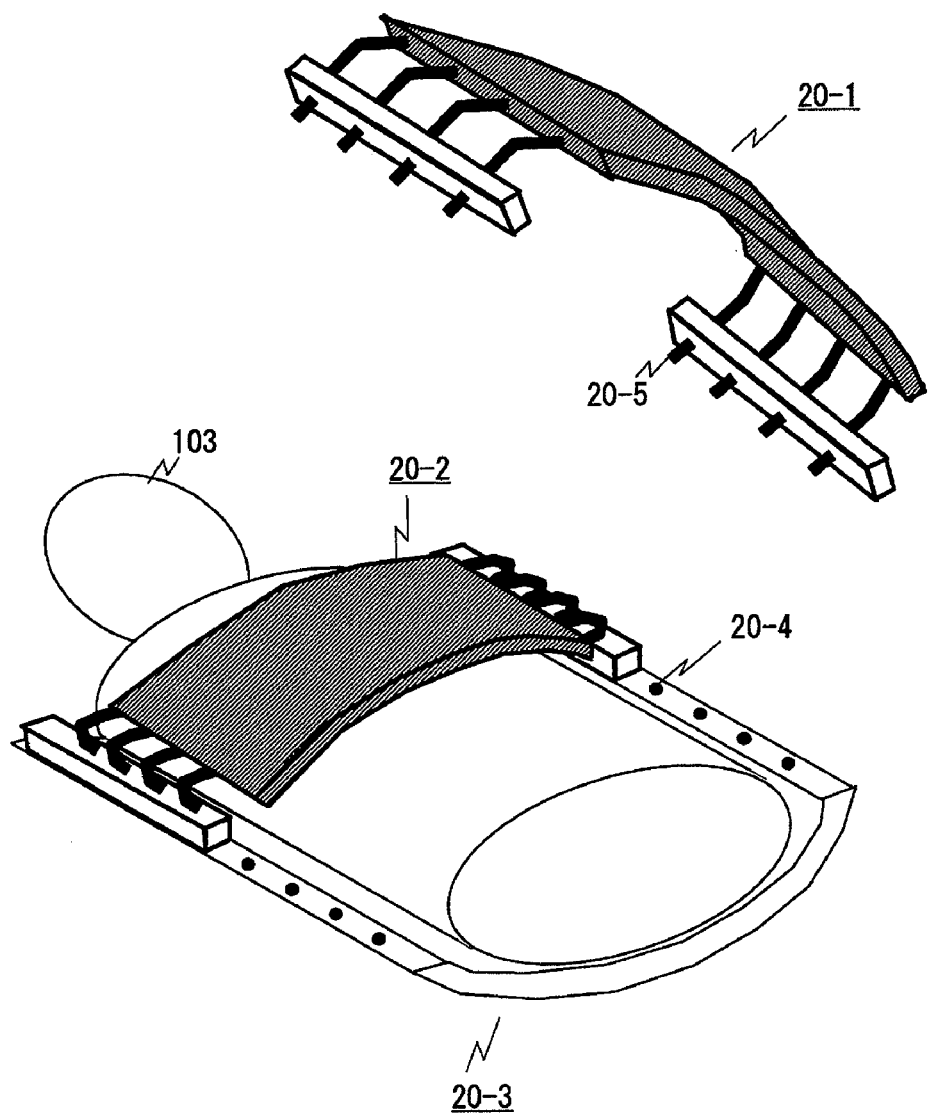
FIG. 20 is a perspective view illustrating a case where the receiver coil of the present invention is disassembled.
Figure 21:
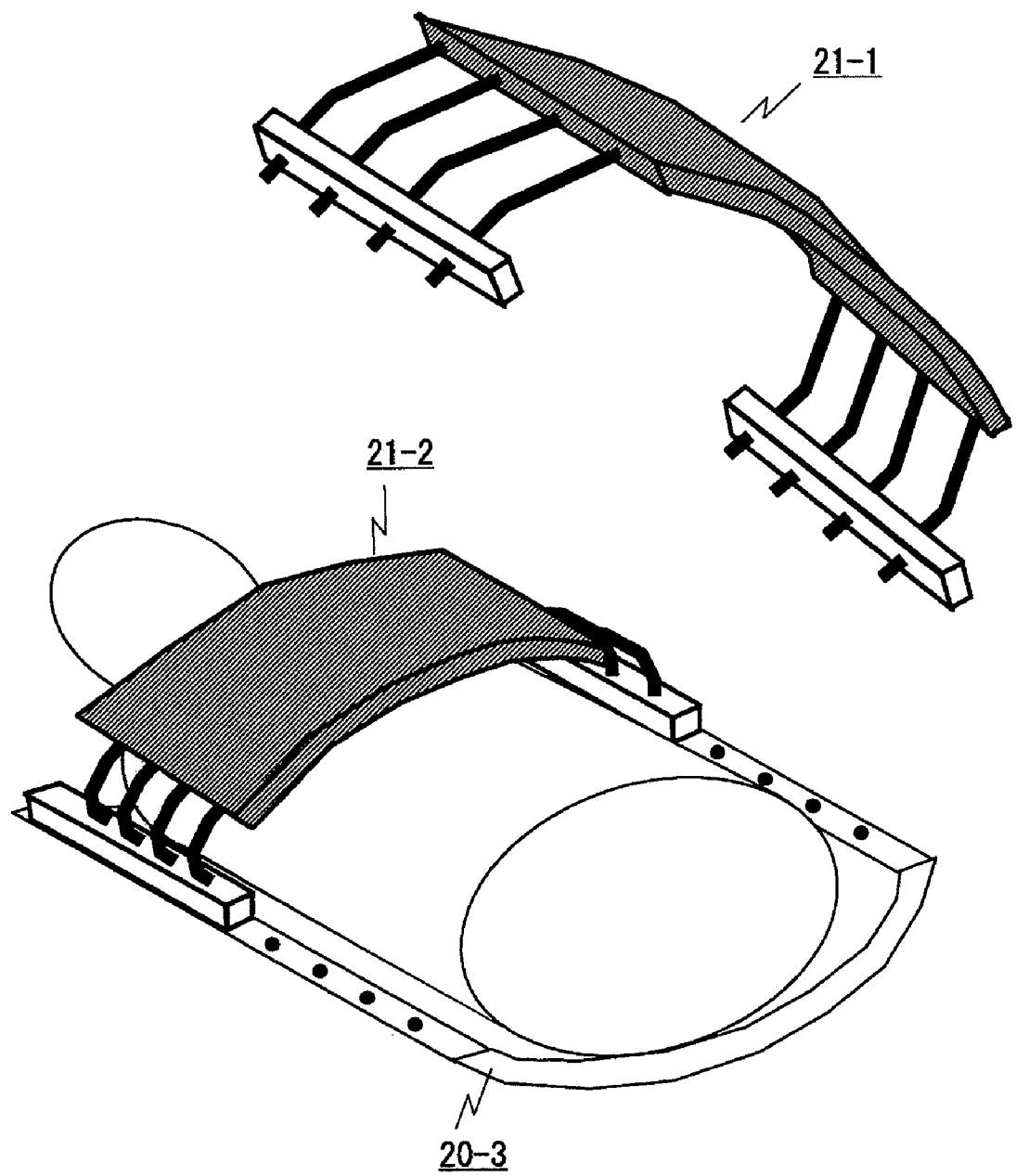
FIG. 21 is a perspective view illustrating a case where the receiver coil of the present invention is disassembled.

Next, an explanation will be made as to an embodiment of a structure of the MRI apparatus that incorporates the receiver coil described above. FIG. 20 illustrates a configuration of the receiver coil, which can be disassembled into chest side parts 20-1 and 20-2, and a backside part 20-3. The coil parts 20-1 and 20-2 are further made up of multiple separated coils. While the subject 103 is placed on the backside 20-3, the coil parts 20-1 and 20-2 are joined to the coil part on the backside 20-3, via connectors 20-4 and 20-5. The coil part on the backside 20-3 are commonly used, and more than one types of coil parts 21-1 and 21-2 having different sizes as shown in FIG. 21 are prepared to be used as the chest side coil parts 20-1 and 20-2. With this configuration, various sizes of test objects can be addressed.

Figure 2:
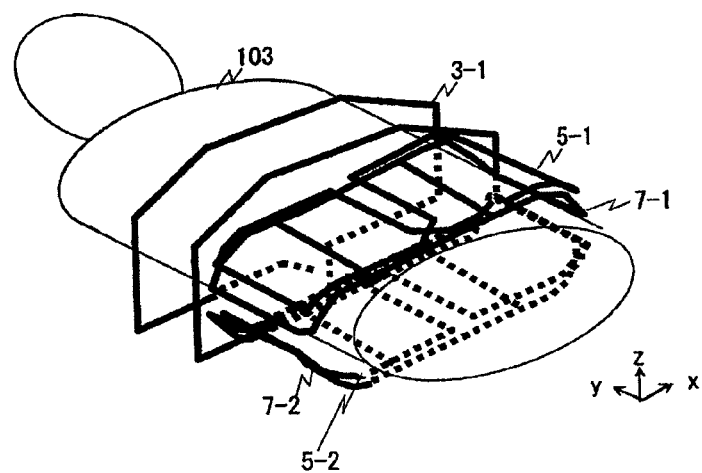
FIG. 2 illustrates a first embodiment of a receiver coil according to the present invention.
Figure 22:
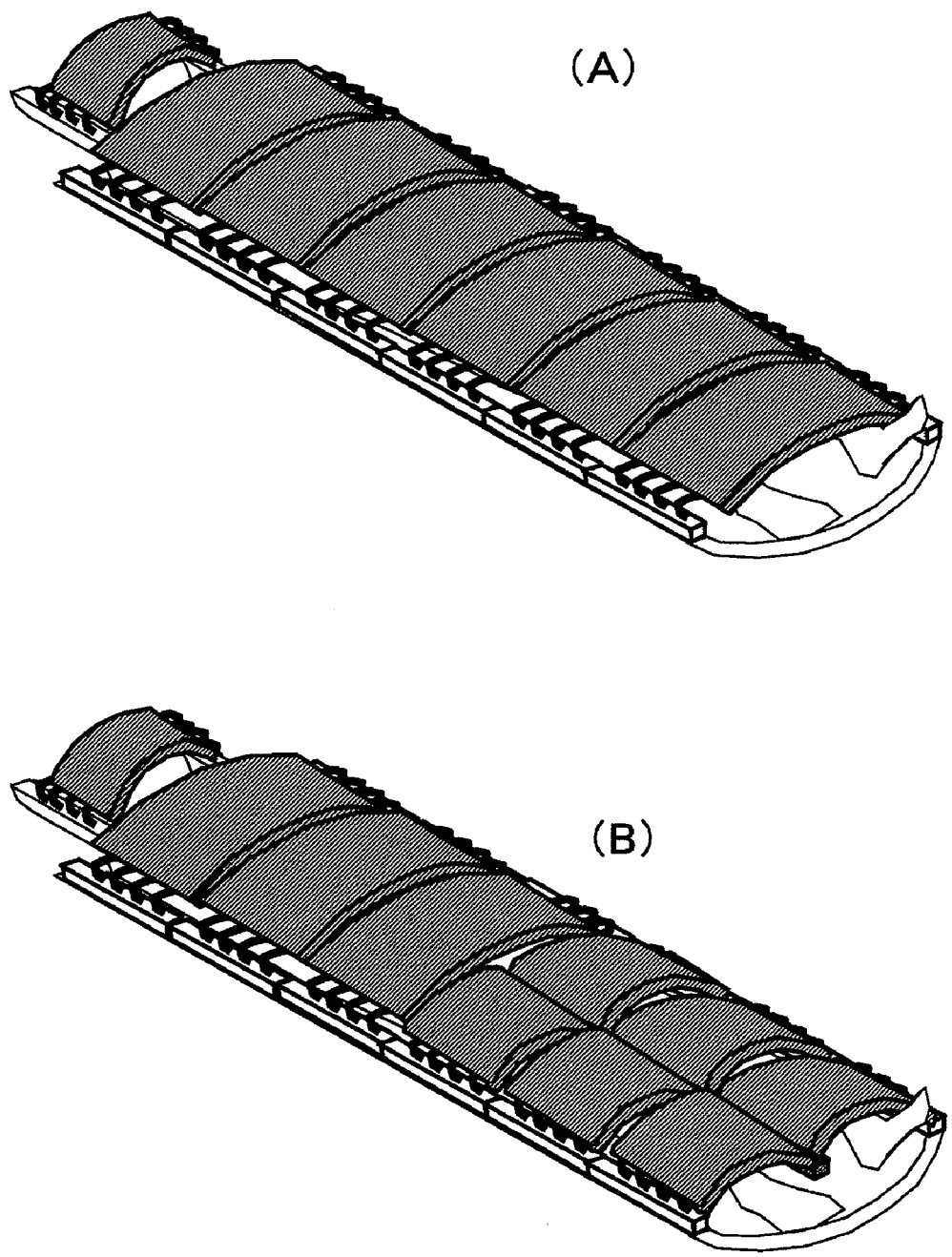
FIG. 22 is a perspective view illustrating a case where the receiver coil of the present invention is placed on the whole body.

One unit based on which the chest side coil is divided is not particularly restricted. By way of example, it may be separated into blocks each having the unit as shown in FIG. 2. For this case, the receiver coil of the present invention may be used as a local coil made up of one block, or used as a wide-field coil or a whole body coil. FIG. 22(A) shows a state where the receiver coil that can be disassembled is placed as the whole body use coil. Such whole body coil is suitable for imaging a wide field while moving abed. In this situation, a high sensitive image can be obtained even when a phase encoding direction and a readout direction are set in any optional direction.

As shown in FIG. 22(B), in another modified example of the present embodiment, the part covering the feet of the subject 103 may be laterally separated.

Figure 23:
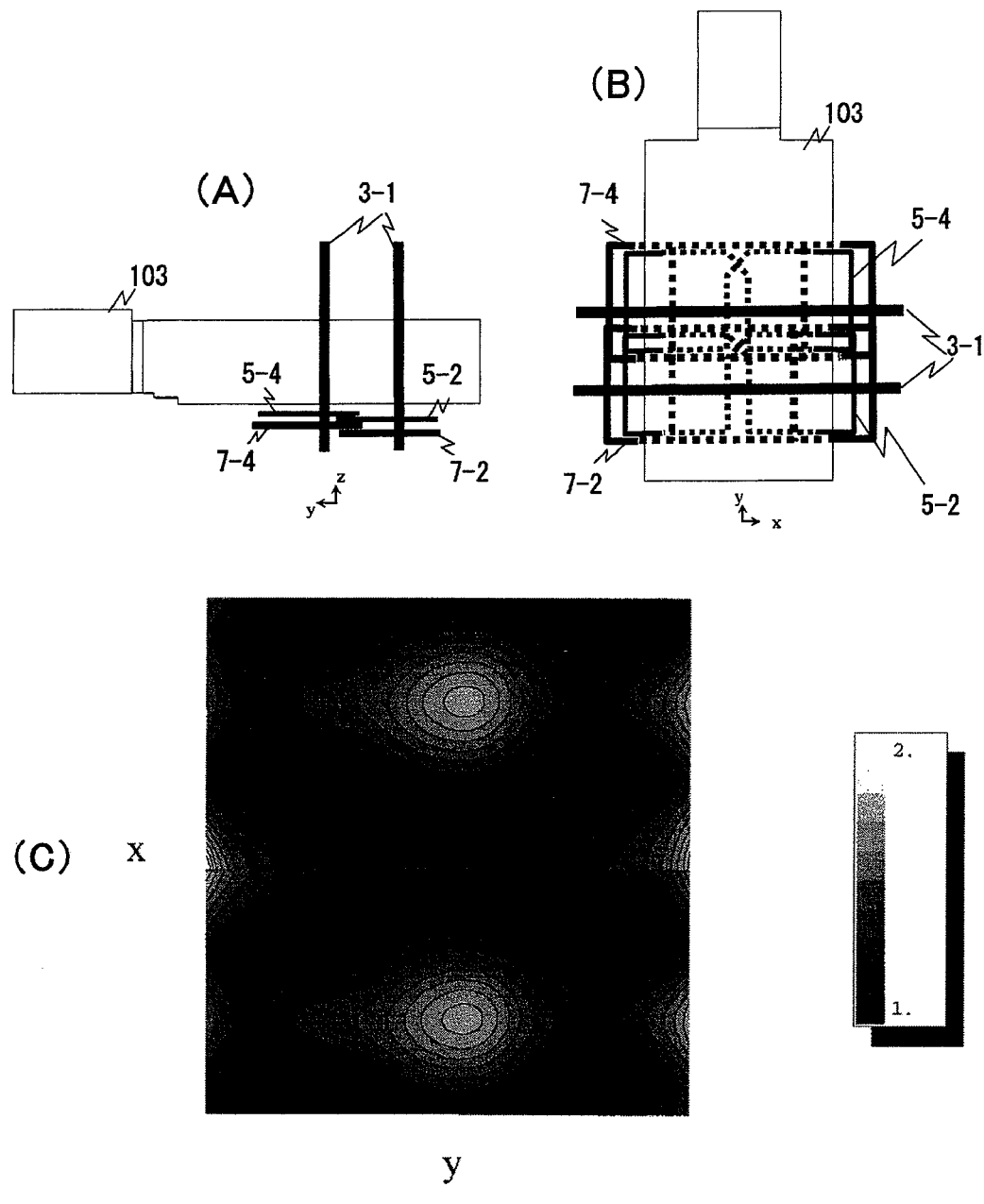
FIG. 23 illustrates a result of simulation as to the g-factor of the receiver coil according to the present invention.

Next, an explanation will be made regarding a result of simulation as an effect of the receiver coil, which is incorporated in the MRI apparatus according to the present invention. FIG. 23(A) and (B), FIG. 24(A) and (B), and FIG. 25(A) and (B) each illustrate a configuration of the receiver coil used in the simulation. The receiver coils shown in FIG. 23 and FIG. 24 use the solenoid coil 3-1 shown in FIG. 3A as the first coil, the butterfly coils 5-2 and 5-4 having two current loops shown in FIG. 3(B) as the second coil, and the coils 7-2, 7-4, and 7-6 having three current loops shown in FIG. 3(C) as the third coil. The solenoid coil 3-1 is arranged in such a manner that the current loops are directed to the static magnetic field and the outer circumference of the subject 103 (phantom) is surrounded. Two butterfly coils 5-2 and 5-4, and the coils 7-2, 7-4, and 7-6 are arranged in such a manner that the current loops of the same type are overlapped by around 10% of area, respectively, and arranged in proximity to one surface of the subject 103 so that the array of the adjacent current loops is placed in the x-direction. In addition, the butterfly coils 5-2 and 5-4, and the coils 7-2, 7-4, and 7-6 are arranged in the x-direction, in such a manner that two areas where the sensitivities of the coils 7-2, 7-4, and 7-6 are maximized are superimposed by the two areas where the sensitivities of the butterfly coils 5-2 and 5-4 are minimized. As for the receiver coil shown in FIG. 23, the butterfly coils 5-2 and 5-4 and the coils 7-2 and 7-4 are superimposed on one another approximately aligned vertically. On the other hand, as for the receiver coil shown in FIG. 24, the current loops of the butterfly coils 5-2 and 5-4 and the coils 7-2, 7-4, and 7-6 are arranged with a displacement in the y-direction, corresponding to half-length of the loop.

Figure 24:
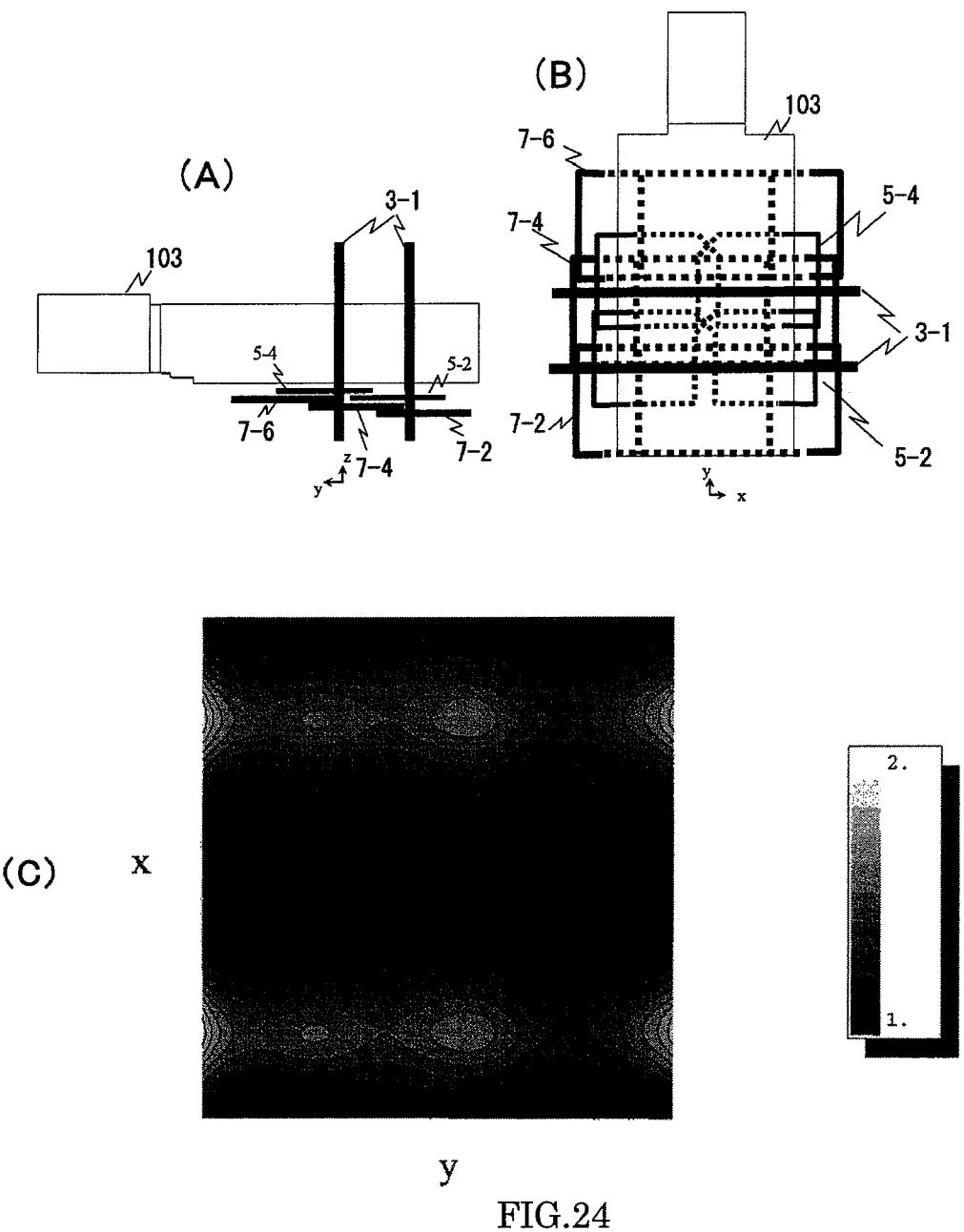
FIG. 24 illustrates a result of simulation as to the g-factor of the receiver coil according to the present invention.
Figure 25:
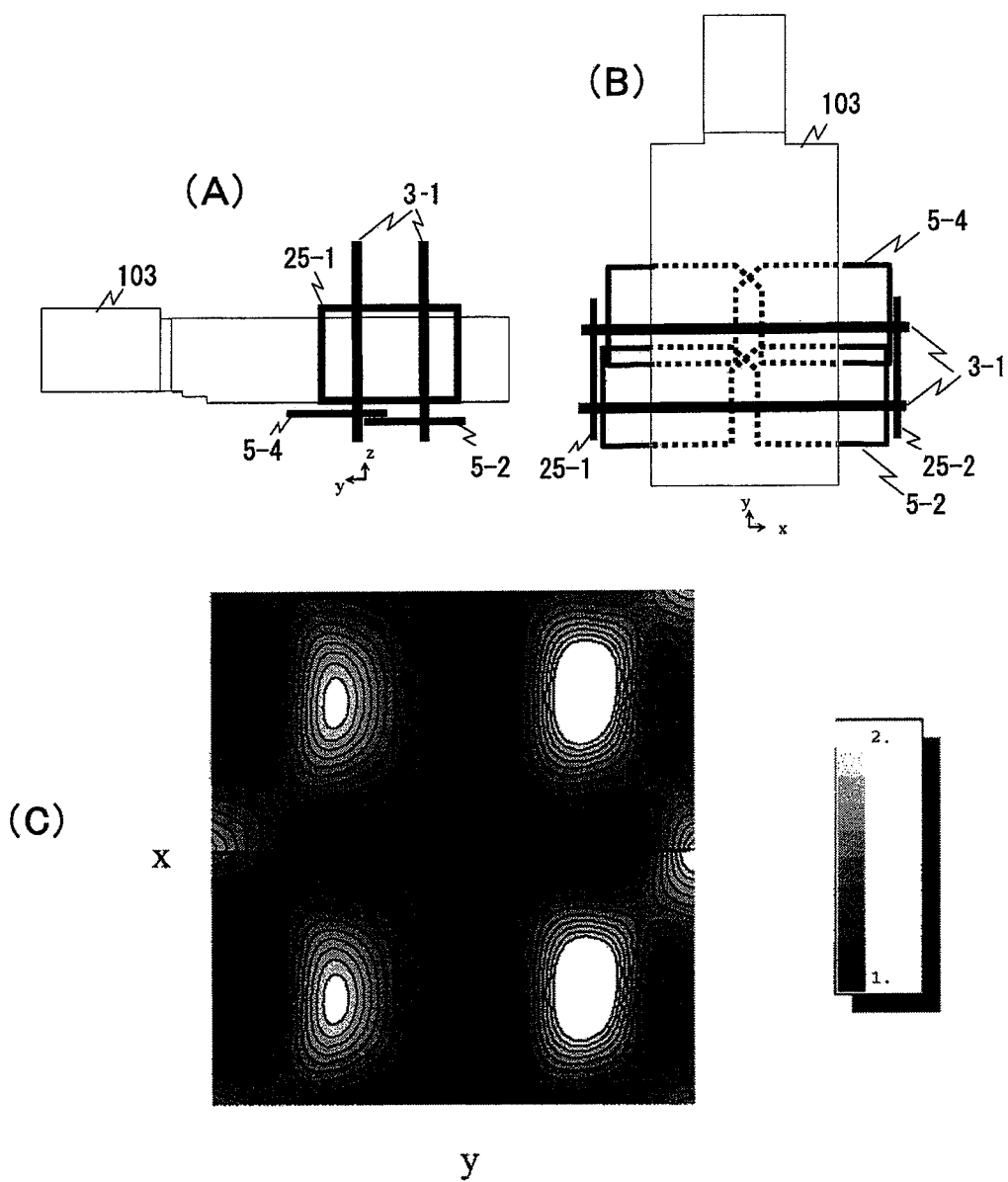
FIG. 25 illustrates a result of simulation as to the g-factor of the receiver coil of the comparative example.
Figure 26:
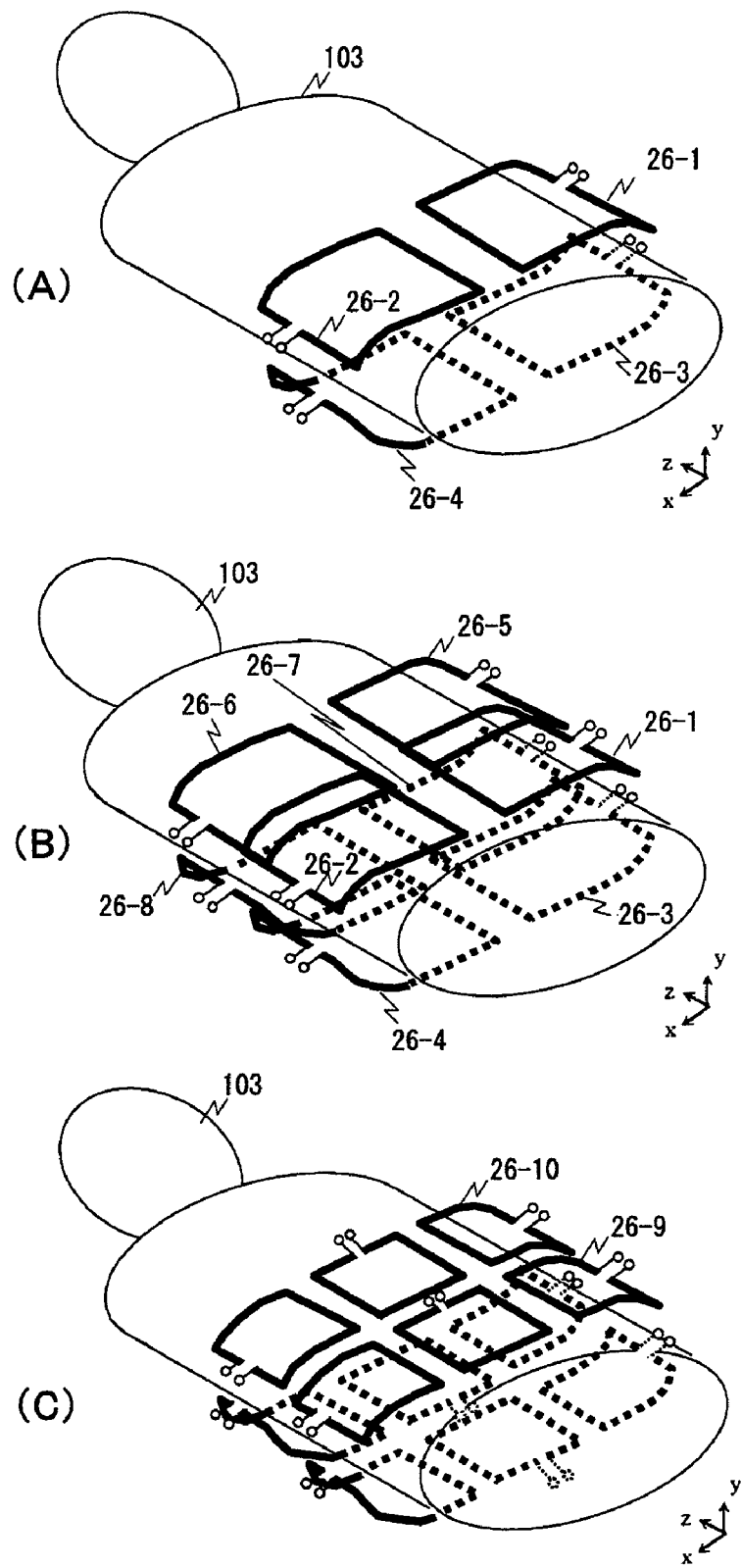
FIG. 26 illustrates arrangement examples of a conventional receiver coil used for a horizontal magnetic field type MRI.

The receiver coil shown in FIG. 25 uses the solenoid coil 3-1 shown in FIG. 3(A) as the first coil, uses the butterfly coils 5-2 and 5-4 having two current loops shown in FIG. 3(B) as the second coil, and this configuration is the same as the receiver coil shown in FIG. 23 and FIG. 24. If only the coil 3-1 and the coils 5-2 and 5-4 are used, multiple coils having different sensitivities in the x-direction do not exist, and therefore the g-factor may become extremely large when the x-direction is selected as the phase encoding direction. Therefore, in the receiver coil shown in FIG. 25, a pair of one-turn solenoid coils 25-1 and 25-2 are arranged respectively on the side surfaces (x-direction) of the subject, the one-turn solenoid coils intersecting the current loop plane of the first coil and intersecting the current loop plane of the second coil.

FIG. 23(C), FIG. 24(C), and FIG. 25(C) respectively illustrate results of the simulation of the g-factor, as to the three receiver coils shown in FIG. 23 to FIG. 25, when the x-direction is selected as the phase encoding direction in a coronal section (xy plane), which is close to the back side of the subject. In the figures, an area illustrated in black color indicates an area having small g-factor (from 1 to 1.1), and an area illustrated in white color indicates an area having large g-factor (at least 2). It is to be noted here that in the receiver coil according to the present invention, more than one surface coils (coils 5-2, 5-4, 7-2, 7-4, and 7-6) are arranged in the z-direction and y-direction. Therefore, if any of these directions is selected as the phase encoding direction, the g-factor becomes small. Here in this example, the simulation has been done to check whether or not the G-factor is improved, when the x-direction is selected as the phase encoding direction.

As shown in FIG. 25(C), it is found that as for the receiver coil having two solenoid coils arranged in the x-direction without using the third coil, there are four areas having extremely large g-factor near the imaging section center. These four areas correspond to the areas showing minimum sensitivity around the centers of the two current loops of the coils 5-2 and 5-4. There is a problem that the S/N ratio of the pickup image may be dramatically deteriorated in those areas. According to this result, it is found that even if loop type coils are arranged in the lateral direction of the subject (x-direction) as multiple coils having different sensitivities in the x-direction, it is not possible to avoid the deterioration of the g-factor on the areas where the sensitivities of the coils 5-2 and 5-4 are minimized.

On the other hand, in the receiver coil of FIG. 23, as shown in FIG. 23(C), it is found that the g-factor is improved compared to the receiver coil of FIG. 25. The four areas where the sensitivities of the coils 5-2 and 5-4 are minimized do not include an area where the g-factor is more than 2. It is found that in the receiving coil shown in FIG. 24, the g-f actor is further improved. Here, the receiving coil includes the second coils 5-2 and 5-4 and the third coils 7-2, 7-4, and 7-6 which are arranged with displacement in the y-direction by half-length of the coil.

INDUSTRIAL APPLICABILITY

The MRI apparatus according to the present invention is provided with a vertical magnetic field use receiver coil, which is made up of a combination of sub-coils having sensitivities different respectively in x, y, and z directions. Therefore, this apparatus enables a speed-up of imaging in picking up an image of an optional section of a wide area such as a whole body.

What is claimed is:

1. An inspection apparatus using magnetic resonance, comprising, a unit for generating a static magnetic field in a vertical direction, a unit for generating an excitation RF pulse that is applied to a test object placed in the static magnetic field, a unit for generating a magnetic field gradient that is superimposed on the static magnetic field, a receiver coil that is made up of multiple sub-coils and that detects a nuclear magnetic resonance signal generated from the subject, the multiple sub-coils further comprising,
   a first coil that is placed in a plane including an axis parallel to a direction of the static magnetic field, and produces a current loop around an outer circumference of the test object,
   a second coil that produces even-numbered current loops in a plane intersecting the plane of the current loop of the first coil, and
   a third coil that produces odd-numbered current loops in a plane approximately parallel to the plane of the current loops of the second coil, wherein, the second coil and the third coil are arranged in such a manner that an array direction of the current loops produced by the second coil is equal to the array direction of the current loops produced by the third coil, and in the array direction of the current loops, a position where a sensitivity of the second coil is minimized approximately coincides with a position where the sensitivity of the third coil is maximized.

2. The inspection apparatus using magnetic resonance, according to claim 1, wherein,
more than one sub-coils of at least either of the second coil and the third coil, are arranged in a direction intersecting the array direction of the current loops.

3. The inspection apparatus using magnetic resonance, according to claim 1, wherein,
the sub-coils of at least either of the second coil and the third coil are arranged in two approximately parallel planes, placing the test object therebetween.

4. The inspection apparatus using magnetic resonance, according to claim 3, wherein,
sub-coils in pairs placed in the approximately parallel planes putting the test object therebetween are arranged at positions displaced from each other, with respect to an axis orthogonal to the array direction of the current loops.

5. The inspection apparatus using magnetic resonance, according to claim 1, wherein,
the second coil and the third coil are arranged so that the current loops thereof are displaced from each other in the direction orthogonal to the array direction of the current loops.

6. The inspection apparatus using magnetic resonance, according to claim 1, wherein,
the second coil includes two current loops, and the third coil includes three current loops.

7. The inspection apparatus using magnetic resonance, according to claim 1, wherein,
the receiver coil includes as the sub-coils, a fourth coil that forms current loops respectively on multiple planes parallel to the plane of the current loop of the first coil.

8. The inspection apparatus using magnetic resonance, according to claim 1, wherein,
a plurality of first coils are arranged in a direction orthogonal to the plane of the current loop of the first coil.

9. The inspection apparatus using magnetic resonance, according to claim 8, wherein,
the receiver coil includes a unit to electromagnetically disconnect each of the plurality of first coils.

10. An inspection apparatus using magnetic resonance, comprising, a unit for generating a static magnetic field in a vertical direction, a unit for generating an excitation RF pulse that is applied to a test object placed in the static magnetic field, a unit for generating a magnetic field gradient that is superimposed on the static magnetic field, a receiver coil that is made up of multiple sub-coils and that detects a nuclear magnetic resonance signal generated from the test object, the multiple sub-coils further comprising,
a first coil that is placed in a plane including an axis parallel to a direction of the static magnetic field, and produces a current loop around the outer circumference of the test object,
a second coil that produces even-numbered current loops in a plane intersecting the plane of the current loop of the first coil, and
a third coil that produces odd-numbered current loops in a plane approximately parallel to the plane of the current loops of the second coil, wherein,
the second coil and the third coil are arranged in such a manner as having an approximately identical array direction of the current loops, and with respect to the array direction, centers of the current loops are alternately placed.

11. The inspection apparatus using magnetic resonance, according to claim 10, wherein,
a plurality of first coils are arranged in a direction orthogonal to the plane of the current loop of the first coil.

12. The inspection apparatus using magnetic resonance, according to claim 11, wherein,
the receiver coil includes a unit to electromagnetically disconnect each of the plurality of first coils.

13. A nuclear magnetic resonance signal receiver coil, comprising,
a first coil that is placed in a plane including an axis parallel to a direction of a static magnetic field applied from outside, and produces a current loop around an outer circumference of a test object,
a second coil that produces even-numbered current loops in a plane intersecting the plane of the current loop of first coil, and
a third coil that produces odd-numbered current loops in a plane approximately parallel to the plane of the current loops of the second coil, wherein,
the second coil and the third coil are arranged in such a manner that an array direction of the current loops produced by the second coil is equal to the array direction of the current loops produced by the third coil, and in the array direction of the current loops, a position where a sensitivity of the second coil is minimized approximately coincides with a position where the sensitivity of the third coil is maximized.

14. A nuclear magnetic resonance signal receiver coil, comprising,
a first coil that is placed in a plane including an axis parallel to a direction of a static magnetic field applied from outside, and produces a current loop around an outer circumference of a test object,
a second coil that produces even-numbered current loops in a plane intersecting the plane of the current loop of the first coil, and
a third coil that produces odd-numbered current loops in a plane approximately parallel to the plane of the current loops of the second coil, wherein,
the second coil and the third coil are arranged in such a manner as having an approximately identical array direction of the current loops, and with respect to the array direction, centers of the current loops are alternately placed.

* * * * *